(12) United States Patent
Maltz et al.

(10) Patent No.: US 11,951,333 B2
(45) Date of Patent: Apr. 9, 2024

(54) X-RAY IMAGING SYSTEM FOR RADIATION THERAPY

(71) Applicant: SHANGHAI UNITED IMAGING HEALTHCARE CO., LTD., Shanghai (CN)

(72) Inventors: Jonathan Maltz, Houston, TX (US); Cheng Ni, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 18/180,818

(22) Filed: Mar. 8, 2023

(65) Prior Publication Data

US 2023/0241419 A1   Aug. 3, 2023

Related U.S. Application Data

(63) Continuation of application No. PCT/CN2021/080638, filed on Mar. 12, 2021, which
(Continued)

(30) Foreign Application Priority Data

Nov. 7, 2020 (CN) .......... 202011234813.9
Nov. 13, 2020 (CN) .......... 202011271345.2
Dec. 14, 2020 (CN) .......... 202011468108.5

(51) Int. Cl.
*A61N 5/10* (2006.01)
*A61B 6/00* (2006.01)
*A61B 6/40* (2024.01)

(52) U.S. Cl.
CPC .......... *A61N 5/1081* (2013.01); *A61B 6/4014* (2013.01); *A61B 6/4435* (2013.01); *A61N 5/1037* (2013.01); *A61N 5/1039* (2013.01)

(58) Field of Classification Search
None
See application file for complete search history.

(56) References Cited

U.S. PATENT DOCUMENTS

| 9,974,494 B2 | 5/2018 | Mostafavi et al. |
| 2003/0048868 A1 | 3/2003 | Bailey et al. |

(Continued)

FOREIGN PATENT DOCUMENTS

| CN | 107184225 A | 9/2017 |
| CN | 107550512 A | 1/2018 |

(Continued)

OTHER PUBLICATIONS

International Search Report in PCT/CN2021/080638 dated Jun. 10, 2021, 5 pages.

(Continued)

*Primary Examiner* — Hoon K Song
(74) *Attorney, Agent, or Firm* — METIS IP LLC

(57) ABSTRACT

A radiation system may include a treatment head configured to deliver a treatment beam to an object, a first assistance assembly configured to facilitate a delivery of the treatment beam, a first imaging radiation source configured to direct a first imaging beam toward the object, a first detector configured to detect at least a portion of the first imaging beam, and a second assistance assembly configured to facilitate a delivery of the first imaging beam. The gantry may include a first gantry portion having a rotation axis and a second gantry portion located next to the first gantry portion along the rotation axis. The treatment head, the first imaging radiation source, and the first detector may be disposed on the first gantry portion. The first assistance assembly and the second assistance assembly may be housed within the second gantry portion.

20 Claims, 18 Drawing Sheets

Related U.S. Application Data is a continuation-in-part of application No. 17/015,033, filed on Sep. 8, 2020.

(56) References Cited

U.S. PATENT DOCUMENTS

| | | |
|---|---|---|
| 2006/0074304 A1 | 4/2006 | Sayeh |
| 2007/0003007 A1 | 1/2007 | Carrano et al. |
| 2007/0003021 A1* | 1/2007 | Guertin ............... A61B 6/4085 378/208 |
| 2007/0003123 A1 | 1/2007 | Fu et al. |
| 2007/0016014 A1 | 1/2007 | Hara et al. |
| 2008/0002809 A1 | 1/2008 | Bodduluri |
| 2008/0205588 A1 | 8/2008 | Kim |
| 2010/0290586 A1* | 11/2010 | Friedrich ............. A61B 6/4014 378/65 |
| 2011/0040170 A1 | 2/2011 | Geva et al. |
| 2011/0182410 A1 | 7/2011 | Balakin |
| 2012/0129360 A1 | 5/2012 | Angerpointner et al. |
| 2013/0256551 A1 | 10/2013 | Yao |
| 2014/0247919 A1 | 9/2014 | Zhang et al. |
| 2017/0106208 A1 | 4/2017 | Gauthier et al. |
| 2017/0189720 A1 | 7/2017 | Liu et al. |
| 2018/0192978 A1 | 7/2018 | Naylor et al. |
| 2019/0168025 A1 | 6/2019 | Koponen et al. |
| 2019/0175945 A1 | 6/2019 | Yan et al. |
| 2019/0209868 A1 | 7/2019 | Stahl et al. |
| 2019/0209869 A1 | 7/2019 | Liu et al. |
| 2019/0336793 A1 | 11/2019 | Zhou et al. |
| 2019/0336795 A1 | 11/2019 | Zhou et al. |
| 2019/0380666 A1 | 12/2019 | Sheng et al. |
| 2020/0170591 A1* | 6/2020 | Gagnon ................. A61B 6/027 |
| 2020/0406064 A1 | 12/2020 | Maltz et al. |

FOREIGN PATENT DOCUMENTS

| | | |
|---|---|---|
| CN | 207765764 U | 8/2018 |
| CN | 108514694 A | 9/2018 |
| CN | 109224320 A | 1/2019 |
| CN | 111093764 A | 5/2020 |
| CN | 111629781 A | 9/2020 |
| CN | 214013363 U | 8/2021 |
| CN | 215605797 U | 1/2022 |
| EP | 3056245 A1 | 8/2016 |
| WO | 2012055098 A1 | 5/2012 |
| WO | 2012099747 A2 | 7/2012 |
| WO | 2018093933 A1 | 5/2018 |
| WO | 2018176016 A1 | 9/2018 |

OTHER PUBLICATIONS

Written Opinion in PCT/CN2021/080638 dated Jun. 10, 2021, 5 pages.
International Search Report in PCT/CN2021/110163 dated Sep. 28, 2021, 5 pages.
Written Opinion in PCT/CN2021/110163 dated Sep. 28, 2021, 6 pages.
International Search Report in PCT/CN2021/138130 mailed on Mar. 11, 2022, 5 pages.
Written Opinion in PCT/CN2021/138130 mailed on Mar. 11, 2022, 5 pages.

* cited by examiner

X-RAY IMAGING SYSTEM FOR RADIATION THERAPY

CROSS-REFERENCE TO THE RELATED APPLICATIONS

This application is a continuation of International Application No. PCT/CN2021/080638, filed on Mar. 12, 2021, which claims priority of U.S. patent application Ser. No. 17/015,033 filed on Sep. 8, 2020, Chinese Application No. 202011234813.9 filed on Nov. 7, 2020, Chinese Application No. CN202011271345.2 filed on Nov. 13, 2020, and Chinese Application No. CN202011468108.5 filed on Dec. 14, 2020, the contents of each of which are hereby incorporated by reference.

TECHNICAL FIELD

The present disclosure generally relates to medical technology, and more particularly, systems and methods for imaging systems for radiation therapy.

BACKGROUND

Radiation therapy is a localized treatment for a specific target tissue (a target volume), such as a cancerous tumor. Dosimetric and geometric data are checked before, after, or during the treatment, to ensure correct patient placement and that the administered radiotherapy treatment matches the previously planned treatment. This process is referred to as image-guided radiation therapy (IGRT), and involves the use of an imaging system to view target tissues while radiation treatment is delivered to the target volume.

SUMMARY

According to an aspect of the present disclosure, a system may be provided. The system may include: a treatment assembly including a treatment head configured to deliver a treatment beam to an object and a first assistance assembly configured to facilitate a delivery of the treatment beam; an imaging assembly including a first imaging radiation source configured to direct a first imaging beam toward the object, a first detector configured to detect at least a portion of the first imaging beam, and a second assistance assembly configured to facilitate a delivery of the first imaging beam; a gantry including a first gantry portion and a second gantry portion. The treatment head, the first imaging radiation source, and the first detector may be disposed on the first gantry portion. The first gantry portion may have a rotation axis. The first gantry portion may rotate about the rotation axis. The second gantry portion may be located next to the first gantry portion along the rotation axis. The first assistance assembly and the second assistance assembly may be housed within the second gantry portion.

In some embodiments, the treatment head, the first imaging radiation source, and the first detector may be configured to rotate in a same rotation plane perpendicular to the rotation axis.

In some embodiments, the treatment head may be configured to rotate in a first rotation plane perpendicular to the rotation axis. The first imaging radiation source and the first detector may be configured to rotate in a second rotation plane that is perpendicular to the rotation axis. The first rotation plane may be different from the second rotation plane.

In some embodiments, the first imaging radiation source and the first detector may be located between the second gantry portion and the treatment head.

In some embodiments, the first imaging radiation source may be located as close as possible to the treatment head without interference with the treatment beam.

In some embodiments, the delivery of the treatment beam and the delivery of the first imaging beam may alternate.

In some embodiments, the first gantry portion may rotate at a first speed when the first imaging beam is delivered. The first gantry portion may rotate at a second speed when the treatment beam is delivered. The first speed may be faster than the second speed.

In some embodiments, the delivery of the treatment beam and the delivery of the first imaging beam may be concurrent.

In some embodiments, the first imaging radiation source, the first detector, and the treatment head may rotate at a third speed when the first imaging beam and the treatment beam are delivered.

In some embodiments, there may be an angular offset between the first imaging radiation source and the treatment head.

In some embodiments, the imaging assembly may include at least one second imaging radiation source each of which is configured to emit a second imaging beam towards the object and at least one second detector configured to detect at least a portion of the at least one second imaging beam. The at least one second imaging radiation source and the at least one second detector may be mounted on the first gantry portion.

In some embodiments, at least one of the at least one second imaging radiation source and the treatment head may be configured to rotate in a same rotation plane perpendicular to the rotation axis.

In some embodiments, at least one of the at least one second imaging radiation source and the treatment head may be configured to rotate in different rotation planes each of which is perpendicular to the rotation axis.

In some embodiments, two of the at least one second imaging radiation source may be respectively located on two sides of the treatment head along the rotation axis.

In some embodiments, at least one of the at least one second imaging radiation source may be configured for two-dimensional (2D) imaging of the object.

In some embodiments, the first assistance assembly may include at least one of a microwave device configured to facilitate the delivery of the treatment beam, an acceleration device configured to accelerate an electron beam to generate the treatment beam, or a first cooling device configured to cool at least one component of the treatment assembly.

In some embodiments, the second assistance assembly may include a high-voltage device configured to facilitate the delivery of the first imaging beam or a second cooling device configured to cool at least one component of the imaging assembly.

In some embodiments, the first imaging radiation source may include a computed tomography (CT) source, and the first detector may include a CT detector.

In some embodiments, the first imaging radiation source may be positioned apart from the treatment head by a certain distance along the rotation axis such that the first imaging radiation source delivers the first imaging beam to image a first region of the object while the treatment head is delivering the treatment beam towards a second region of the object.

In some embodiments, the first region may relate to a motion of the second region.

In some embodiments, the motion of the second region may be determined based on an image of the first region.

In some embodiments, the treatment assembly may include a collimator. The collimator may include a plurality of leaves forming an aperture that is configured to collimate the treatment beam to conform to a target region of the object to be treated.

In some embodiments, when the object is moved along the rotation axis relative to the treatment head, at least one of a position or a shape of the aperture may be adjusted such that the collimated treatment beam tracks the target region.

In some embodiments, when the target region of the object to be treated moves due to a motion of an organ of the object, at least one of a position or a shape of the aperture may be adjusted such that the collimated treatment beam tracks the target region of the object to be treated.

In some embodiments, the object may be further moved along the rotation axis to obtain an image of a next target region to be treated.

In some embodiments, the position or the shape of the aperture may be adjusted by at least one of: moving the whole collimator along the rotation axis, or adjusting one or more leaves of the plurality of leaves of the collimator that are involved in forming the aperture.

In some embodiments, the first imaging radiation source and the first detector may be disposed in a first section of the first gantry portion. The treatment head may be disposed in a second section of the first gantry portion. The first section may be configured to rotate independently from the second section.

In some embodiments, the first section may be configured to rotate in a first range without collision with the second section.

In some embodiments, the treatment head may be configured to move radially away from a rotation axis of the gantry to allow the first section to rotate independently in a second range without collision. The second range may be larger than the first range.

In some embodiments, the first section and the second section may be concentrically arranged.

In some embodiments, the first section and the second section may be arranged in parallel along the rotation axis.

In some embodiments, the first imaging radiation source and the first detector may rotate along with the treatment head.

In some embodiments, a distance between an isocenter of the treatment assembly and an isocenter of the imaging assembly may be below a threshold.

In some embodiments, the threshold may be no more than 1 meter.

In some embodiments, the imaging assembly may include a helical computed tomography (CT) or a sequential CT.

According to another aspect of the present disclosure, a method may be provided. The method may include positioning an object in a radiation system. The radiation system may include: a treatment assembly including a treatment head and a first assistance assembly configured to facilitate a delivery of a treatment beam from the treatment head; an imaging assembly including an imaging radiation source, a detector, and a second assistance assembly configured to facilitate a delivery of an imaging beam from the imaging radiation source; and a gantry including a first gantry portion and a second gantry portion. The first gantry portion may have a rotation axis. In some embodiments, the first gantry portion may be configured to rotate about the rotation axis.

The treatment head, the imaging radiation source, and the detector may be mounted on the first gantry portion. The second gantry portion may be located next to the first gantry portion along the rotation axis. The first assistance assembly and the second assistance assembly may be housed within the second gantry portion. The method may also include delivering, from the imaging radiation source, an imaging beam to the object; detecting, by the detector, at least a portion of the imaging beam to generate an imaging dataset; and delivering, from the treatment head, a treatment beam to the object.

In some embodiments, the method may further include generating, based on the imaging dataset, an image associated with the object. The delivering of the treatment beam to the object may be based further on the image.

In some embodiments, the delivering of the treatment beam to the object may further include: adjusting a treatment plan based on the image; and delivering, from the treatment head and based on the adjusted treatment plan, an adjusted treatment beam to the object.

In some embodiments, the delivering of the treatment beam to the object may further include: adjusting a treatment plan based on the image; and causing the treatment head to pause the delivery of the treatment beam.

In some embodiments, the method may further include: determining whether an unpredicted motion of the object exists based on the image; and in response to determining that the unpredicted motion of the object exists, causing the treatment head to pause the delivery of the treatment beam.

In some embodiments, the method may further include: determining whether the object has ceased a planned breathhold based on the image; and in response to determining that the object has ceased the planned breathhold, causing the treatment head to pause the delivery of the treatment beam.

According to yet another aspect of the present disclosure, a non-transitory computer readable medium may be provided. The non-transitory computer readable medium may include instructions being executed by at least one processor and causing the at least one processor to implement a method. The method may include positioning an object in a radiation system. The radiation system may include a treatment assembly, an imaging assembly, and a gantry. The treatment assembly may include a treatment head configured to deliver a treatment beam to an object and a first assistance assembly configured to facilitate a delivery of the treatment beam. The imaging assembly may include a first imaging radiation source configured to direct a first imaging beam toward the object, a first detector configured to detect at least a portion of the first imaging beam, and a second assistance assembly configured to facilitate a delivery of the first imaging beam. The gantry may include a first gantry portion and a second gantry portion. The treatment head, the first imaging radiation source, and the first detector may be disposed on the first gantry portion. The first gantry portion may have a rotation axis. In some embodiments, the first gantry portion may be configured to rotate about the rotation axis. The second gantry portion may be located next to the first gantry portion along the rotation axis. The first assistance assembly and the second assistance assembly may be housed within the second gantry portion. The method may also include delivering, from the imaging radiation source, an imaging beam to the object; detecting, by the detector, at least a portion of the imaging beam to generate an imaging dataset; and delivering, from the treatment head, a treatment beam to the object.

According to yet another aspect of the present disclosure, a system may be provided. The system may include: a treatment assembly including a treatment head configured to deliver a treatment beam to an object and a first assistance assembly configured to facilitate a delivery of the treatment beam; an imaging assembly including a first imaging radiation source configured to direct a first imaging beam toward the object, a first detector configured to detect at least a portion of the first imaging beam, and a second assistance assembly configured to facilitate a delivery of the first imaging beam; and a gantry having a rotation axis and supporting the treatment assembly and the imaging assembly. The treatment head, the first imaging radiation source, and the first detector may be disposed on a same side of the first assistance assembly and the second assistance assembly along the rotation axis.

In some embodiments, the treatment head may be located on one side of the first imaging source along the rotation axis. The first assistance assembly and the second assistance assembly may be located on another side of the first imaging source along the rotation axis.

In some embodiments, the treatment head, the first imaging radiation source, and the first detector may be rotatable with the gantry.

In some embodiments, the treatment head, the first imaging radiation source, and the first detector may be configured to rotate in a same rotation plane that is perpendicular to the rotation axis.

In some embodiments, the treatment head may be configured to rotate in a first rotation plane perpendicular to the rotation axis. The first imaging radiation source and the first detector may be configured to rotate in a second rotation plane that is perpendicular to the rotation axis. The first rotation plane may be different from the second rotation plane.

In some embodiments, the first imaging radiation source may be located as close as possible to the treatment head without interference with the treatment beam.

In some embodiments, the delivery of the treatment beam and the delivery of the first imaging beam may alternate.

In some embodiments, there may be an angular offset between the first imaging radiation source and the treatment head.

In some embodiments, the imaging assembly may include: at least one second imaging radiation source each of which is configured to emit a second imaging beam towards the object and at least one second detector configured to detect at least a portion of the at least one second imaging beam. The at least one second imaging radiation source and the at least one second detector may be mounted on the same side of the first assistance assembly and the second assistance assembly along the rotation axis.

In some embodiments, at least one of the at least one second imaging radiation source and the treatment head may be configured to rotate in a same rotation plane perpendicular to the rotation axis.

In some embodiments, at least one of the at least one second imaging radiation source and the treatment head may be configured to rotate in different rotation planes each of which is perpendicular to the rotation axis.

In some embodiments, two of the at least one second imaging radiation source may be respectively located on two sides of the treatment head along the rotation axis.

In some embodiments, at least one of the at least one second imaging radiation source may be configured for two-dimensional (2D) imaging of the object.

In some embodiments, the first assistance assembly may include at least one of a microwave device configured to facilitate the delivery of the treatment beam, an acceleration device configured to accelerate an electron beam to generate the treatment beam, or a first cooling device configured to cool at least one component of the treatment head assembly.

In some embodiments, the second assistance assembly may include: a high-voltage device configured to facilitate the delivery of the first imaging beam, or a second cooling device configured to cool at least one component of the imaging assembly.

In some embodiments, the first imaging radiation source may include a computed tomography (CT) source. The first detector may include a CT detector.

In some embodiments, the first imaging radiation source may be positioned apart from the treatment head by a certain distance along the rotation axis such that the first imaging radiation source delivers the first imaging beam to image a first region of the object while the treatment head is delivering the treatment beam towards a second region of the object, the first region may relate to a motion of the second region, or the motion of the second region may be determined based on an image of the first region.

In some embodiments, the treatment assembly may include a collimator. The collimator may include a plurality of leaves forming an aperture that is configured to collimate the treatment beam to conform to a target region of the object to be treated.

In some embodiments, when the object is moved along the rotation axis relative to the treatment head, at least one of a position or a shape of the aperture may be adjusted such that the collimated treatment beam tracks the target region.

In some embodiments, when the target region of the object to be treated moves relative to the treatment head due to a motion of an organ of the object, at least one of a position or a shape of the aperture may be adjusted such that the collimated treatment beam tracks the target region of the object to be treated.

In some embodiments, the object may be further moved along the rotation axis to obtain an image of a next target region to be treated.

In some embodiments, the position or the shape of the aperture may be adjusted by at least one of: moving the whole collimator along the rotation axis, or adjusting one or more leaves of the plurality of leaves of the collimator that are involved in forming the aperture.

In some embodiments, the first imaging radiation source and the first detector may be disposed in a first section of the same side of the first assistance assembly and the second assistance assembly. The treatment head may be disposed in a second section of the same side of the first assistance assembly and the second assistance assembly. The first section may be configured to rotate independently from the second section.

In some embodiments, the first section may be configured to rotate in a first range without collision with the second section.

In some embodiments, the treatment head may be configured to move radially away from a rotation axis of the gantry to allow the first section to rotate independently in a second range without collision. The second range may be larger than the first range.

In some embodiments, the first section and the second section may be concentrically arranged.

In some embodiments, the first section and the second section may be arranged in parallel along the rotation axis.

In some embodiments, the first imaging radiation source and the first detector may be rotatable with the treatment head.

In some embodiments, a distance between an isocenter of the treatment assembly and an isocenter of the imaging assembly may be below a threshold.

In some embodiments, the threshold may be no more than 1 meter.

In some embodiments, the imaging assembly may include a helical computed tomography (CT) or a sequential CT.

According to yet another aspect of the present disclosure, a method may be provided. The method may include: causing an object to be positioned in a radiation system, the radiation system including: a treatment assembly including a treatment head configured to deliver a treatment beam to an object and a first assistance assembly configured to facilitate a delivery of the treatment beam; an imaging assembly including a first imaging radiation source configured to direct a first imaging beam toward the object, a first detector configured to detect at least a portion of the first imaging beam, and a second assistance assembly configured to facilitate a delivery of the first imaging beam; gantry having a rotation axis and supporting the treatment assembly and the imaging assembly, the treatment head, the first imaging radiation source, and the first detector being disposed on a same side of the first assistance assembly and the second assistance assembly along the rotation axis; using the imaging radiation source to deliver an imaging beam to the object; obtaining an imaging dataset corresponding to at least a portion of the imaging beam detected by the detector; and causing the treatment head to deliver a treatment beam to the object.

According to yet another aspect of the present disclosure, a non-transitory computer readable medium may be provided. The non-transitory computer readable medium may include instructions being executed by at least one processor and causing the at least one processor to implement a method. The method may include: causing an object to be positioned in a radiation system, the radiation system including: a treatment assembly including a treatment head configured to deliver a treatment beam to an object and a first assistance assembly configured to facilitate a delivery of the treatment beam; an imaging assembly including a first imaging radiation source configured to direct a first imaging beam toward the object, a first detector configured to detect at least a portion of the first imaging beam, and a second assistance assembly configured to facilitate a delivery of the first imaging beam; a gantry having a rotation axis and supporting the treatment assembly and the imaging assembly, the treatment head, the first imaging radiation source, and the first detector being disposed on a same side of the first assistance assembly and the second assistance assembly along the rotation axis; causing the imaging radiation source to deliver an imaging beam to the object; obtaining an imaging dataset corresponding to at least a portion of the imaging beam detected by the detector; and causing the treatment head to deliver a treatment beam to the object.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by other expressions if they achieve the same purpose.

Figure 11:
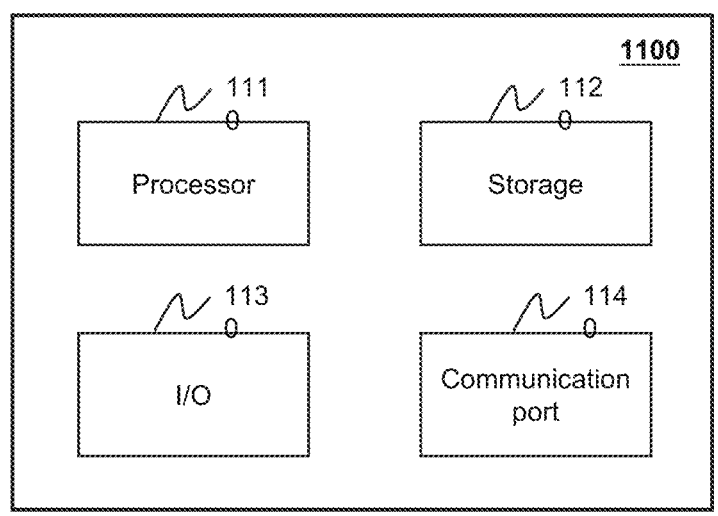
FIG. 11 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 1110 as illustrated in FIG. 11) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

In this present disclosure, the terms "radiation therapy," "radiotherapy," "radiation treatment," and "treatment" may be used interchangeably to refer to a therapy for treating, e.g., cancers and other ailments in biological (e.g., human and animal) tissue using radiation. The terms "treatment plan," "therapy plan," and "radiotherapy plan" may be used interchangeably to refer to a plan used to perform radiotherapy.

An aspect of the present disclosure relates to a radiation system. The radiation system may include a gantry, a treatment assembly, and an imaging assembly. The treatment assembly may include a treatment head and a first assistance assembly configured to facilitate a delivery of a treatment beam by the treatment head. The imaging assembly may include one or more imaging radiation sources, one or more detectors, and a second assistance assembly configured to facilitate a delivery of an imaging beam by the one or more imaging radiation sources. The gantry may include a first gantry portion and a second gantry portion located next to the first gantry portion along a rotation axis. The treatment head, the one or more imaging radiation sources, and the one or more detectors may be disposed on the first gantry portion. The first assistance assembly and the second assistance assembly may be housed within the second gantry portion. By arranging the treatment head, the one or more imaging radiation sources, and the one or more detectors together in the first gantry portion and arranging the first and second assistance assemblies in the second gantry portion, a distance between an isocenter of the treatment assembly and an isocenter of the imaging assembly may be reduced to below a threshold (e.g., 20 centimeters, 40 centimeters, 50 centimeters, 80 centimeters, 1 meter), compared to the configuration in which the treatment assembly is arranged together in a portion of the gantry and the imaging assembly is arranged together in another portion of the gantry. The reduced distance between the isocenter of the treatment assembly and the isocenter of the imaging assembly may obviate the need to move a patient between different positions for imaging and treatment of a target region in the radiation system, or reduce the distance between different positions for imaging and treatment in the radiation system by which the patient needs to be moved, which, in turn, may reduce an error introduced by the movement between different positions for imaging and treatment (e.g., an error caused by different saggings of the patient support (e.g., patient support 113) at different positions in the radiation system) and/or improve the efficiency of imaging/treatment performed using the radiation system.

Figure 1:
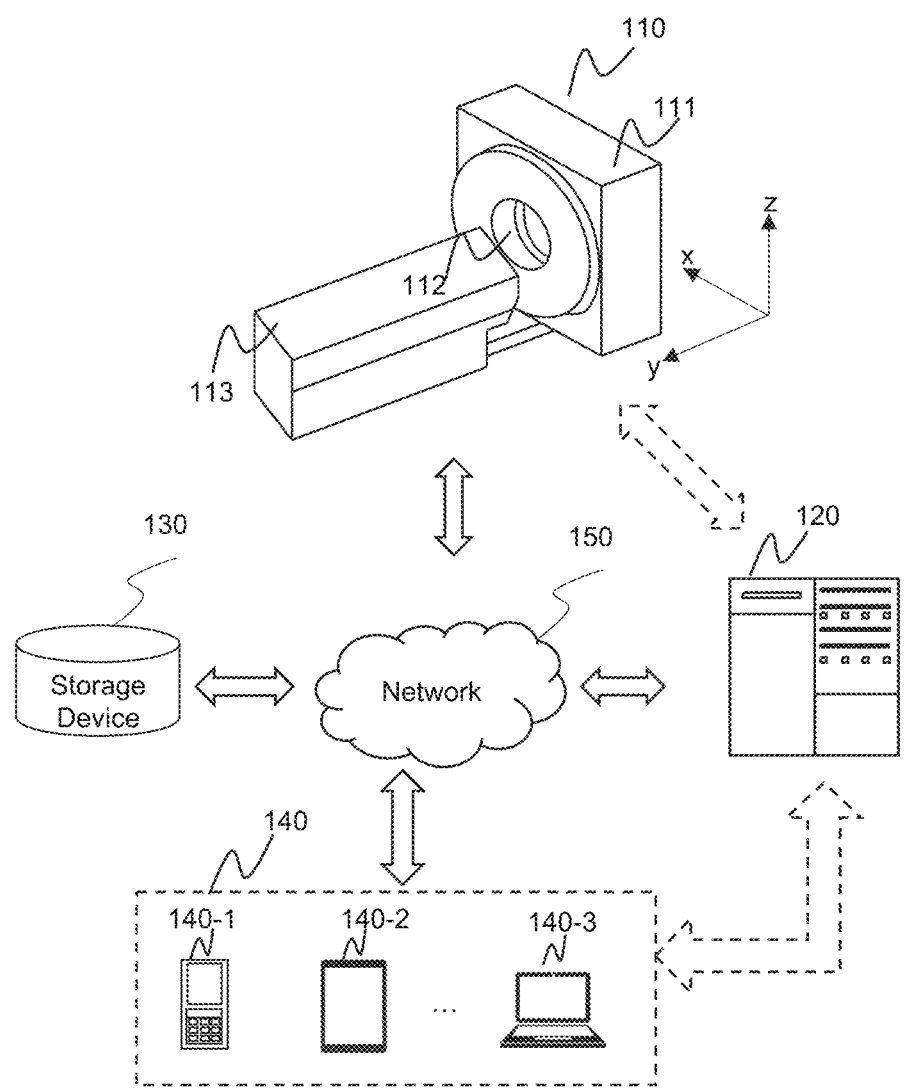
FIG. 1 is a schematic diagram illustrating an exemplary radiation system according to some embodiments of the present disclosure.

FIG. 1 is a schematic diagram illustrating an exemplary radiation system according to some embodiments of the present disclosure. In some embodiments, the radiation system 100 may be configured to provide radiation therapy (e.g., stereotactic radiosurgery and/or precision radiotherapy) for lesions, tumors, and conditions anywhere in a patient where radiation treatment is indicated. In some embodiments, the radiation system 100 may include a treatment plan system (TPS), an image-guided radiotherapy (IGRT) system, etc.

As illustrated in FIG. 1, the radiation system 100 may include a radiation device 110, a processing device 120, a storage device 130, one or more terminals 140, and a network 150. The components in the radiation system 100 may be connected in one or more of various ways. Merely by way of example, the radiation device 110 may be connected to the processing device 120 through the network 150. As another example, the radiation device 110 may be connected to the processing device 120 directly as indicated by the bi-directional arrow in dotted lines linking the radiation device 110 and the processing device 120. As a further example, the storage device 130 may be connected to the processing device 120 directly or through the network 150. As still a further example, the terminal 140 may be connected to the processing device 120 directly (as indicated by the bi-directional arrow in dotted lines linking the terminal 140 and the processing device 120) or through the network 150.

In some embodiments, the radiation system 100 may perform image-guided radiation therapy (IGRT) that monitors, using X-ray imaging, a target volume (e.g., a tumor, a lesion, etc.) (also referred to as a target region) to be treated inside an object (e.g., a patient). In this case, the radiation device 110 may include a treatment assembly (also referred to as a treatment device) and an imaging assembly (also referred to as an imaging device). The treatment assembly may be configured to deliver a treatment beam to the target volume. The imaging assembly may be configured to perform imaging (e.g., two-dimensional (2D) imaging, three-dimensional (3D) imaging, or four-dimensional (4D) imaging) on the target volume and/or normal tissue surrounding the target volume (also referred to as "organ at risk") before, after, or while the radiotherapy is performed. In this way, the anatomy, as well as the motion or deformation, of the target volume can be detected, and the patient's position and/or the treatment beam can be adjusted for more precise radiation dose delivery to the target volume.

In some embodiments, the treatment assembly may include a treatment head 112 and a first assistance assembly. In some embodiments, the treatment head 112 may be configured to deliver a treatment beam to the object to perform a radiation treatment to a target volume inside the object and/or perform imaging on a region of interest (ROI) (e.g., including the target volume and/or organs at risk (OARs)) of the object. For example, the treatment head 112 may include an acceleration device (e.g., an acceleration tube), a treatment source (e.g., an X-ray target), a primary collimator, a filter (e.g., a flattening filter), at least one jaw, a multi-leaf collimator, etc. The treatment head 112 may include an acceleration tube of species of particles including, for example, photons, electrons, protons, or heavy ions, etc. In some embodiments, the treatment beam may include a relatively high energy beam (e.g., an MV beam). In some embodiments, the treatment beam may include a fan beam, a cone beam, or a tetrahedron beam.

In some embodiments, the first assistance assembly may be configured to facilitate a delivery of the treatment beam. The first assistance assembly may include a microwave device configured to facilitate the delivery of the treatment beam, an acceleration device configured to accelerate an electron beam to generate the treatment beam, a first cooling device configured to cool at least one component (e.g., the microwave device, the acceleration device) of the treatment head assembly, or the like, or any combination thereof. The microwave device may be configured to generate an electromagnetic field configured to accelerate an electron beam to generate a high-energy electron beam. For example, the first assistance assembly may include the microwave device, the acceleration device, and the first cooling device. As another example, the first assistance assembly may include the first cooling device, and the microwave device and the acceleration device may be part of the treatment head and rotate along with the treatment head.

In some embodiments, at least one component of the first assistance assembly may rotate along with the treatment head. For example, a first cooling device (e.g., a cooling device whose cooling medium includes a gas (or referred to as a gas cooling device), e.g., air, nitrogen, helium, hydrogen) of the acceleration device may rotate along with the treatment head. As another example, the microwave device may rotate along with the treatment head. As a further example, the whole first assistance assembly may rotate along with the treatment head. In some embodiments, at least one component of the first assistance assembly may be stationary while the other components of the first assistance assembly rotates with the treatment head. For example, a first cooling device (e.g., a cooling device whose cooling medium includes a liquid (or referred to as a liquid cooling device), e.g., water, a water solution, a dielectric fluid, polyalkylene glycol (PAG), an oil) of the acceleration device may be stationary while the microwave device of the first assistance assembly rotates with the treatment head. As another example, the microwave device may be stationary while the acceleration device of the first assistance assembly rotates with the treatment head. As a further example, the whole first assistance assembly may be stationary while the treatment head rotates.

In some embodiments, the imaging device may include one or more imaging radiation sources, one or more detectors, and a second assistance assembly. As used herein, an imaging radiation source may be configured to deliver an imaging beam to the object to perform imaging (e.g., 2D imaging, 3D imaging, or 4D imaging) on the ROI (e.g., including the target volume and/or the OARs) of the object. The imaging beam may include X-rays, γ-rays, α-rays, ultraviolet, RF, radar, laser, neutrons, protons, or the like, or a combination thereof. In some embodiments, the imaging beam may include a relatively low energy beam (e.g., a kV beam). In some embodiments, the imaging beam may include a fan-beam, a cone beam, or a tetrahedron beam.

In some embodiments, the one or more detectors may be configured to detect at least a portion of imaging beam(s) emitted from the one or more imaging radiation sources. For example, the one or more detectors may include a single-row detector or a multi-row detector. As another example, the one or more detectors may include a flat panel detector or a curvilinear detector. In some embodiments, the imaging device may include a computed tomography (CT) device (e.g., a helical CT device, a sequential CT device).

In some embodiments, at least two of the one or more imaging radiation sources may share one of the one or more detectors. The shared detector may be configured to detect at least two imaging beams each from one of the at least two imaging radiation sources. In some embodiments, each of the one or more imaging radiation sources may correspond to one of the one or more detectors. In some embodiments, the one or more imaging radiation sources may include a first imaging radiation source and at least one second imaging radiation source. The one or more detectors may include a first detector corresponding to the first imaging radiation source and at least one second detector corresponding to the at least one second imaging radiation source. The first imaging radiation source may be configured to direct a first imaging beam toward the object. The corresponding first detector may be configured to detect at least a portion of the first imaging beam. An imaging dataset acquired based on the at least a portion of the first imaging beam may be used to generate a 3D image. Each of the at least one second imaging radiation source may be configured to emit a second imaging beam towards the object. The at least one second detector may be configured to detect at least a portion of the at least one second imaging beam. An imaging dataset acquired based on at least a portion of one second imaging beam detected by one of the at least one second detector may be used to generate a 2D image.

In some embodiments, one (also referred to as treatment beam detector) of the at least one second detector may be configured to detect the treatment beam emitted from the treatment head 112 and/or at least a portion of the imaging beam(s) emitted from the one or more imaging radiation sources. For example, the treatment beam detector may include an electronic portal imaging device (EPID). In some embodiments, the treatment beam detector may be static. In some embodiments, the treatment beam detector may move independently of the treatment head 112. In some embodiments, the treatment beam detector may be positioned diametrically opposite to the treatment head 112 and rotate along with the treatment head 112. In some embodiments, the treatment beam detector may be configured to detect kV beams and also MV beams. In some embodiments, the treatment beam detector may be configured to detect kV beams only or MV beams only.

In some embodiments, the second assistance assembly may be configured to facilitate a delivery of the imaging beam. The second assistance assembly may include a high-voltage device configured to facilitate the delivery of the first imaging beam or a second cooling device configured to cool at least one component (e.g., the high-voltage device) of the imaging assembly. The high-voltage device may be configured to generate an electric field to accelerate an electron beam, and the accelerated electron beam may impinge on an anode of the second assistance assembly to generate the first imaging beam. For example, the second assistance assembly may include the high-voltage device and the second cooling device. As another example, the second assistance assembly may include the second cooling device, and the high-voltage device may be separated from the second assistance assembly, for example, located in the first gantry portion, and rotate along with the one or more imaging radiation sources. As a further example, the second assistance assembly may include the high-voltage device, and the second cooling device may be separated from the second assistance assembly, for example, located in the first gantry portion, and rotate along with the one or more imaging radiation sources.

In some embodiments, at least one component of the second assistance assembly may rotate along with the one or more imaging radiation sources. For example, the high-voltage device may rotate along with the one or more imaging radiation sources. As another example, the second cooling device (e.g., a liquid cooling device) (e.g., water, a water solution, a dielectric fluid, polyalkylene glycol (PAG), an oil) may rotate along with the one or more imaging radiation sources. As a further example, the whole second assistance assembly 215 may rotate along with the one or more imaging radiation sources. In some embodiments, at least one component of the second assistance assembly 215 may be stationary while the one or more imaging radiation sources rotate. For example, the second cooling device (e.g., a gas cooling device (e.g., air, nitrogen, helium, hydrogen), a liquid cooling device) may be stationary while the one or more imaging radiation sources rotate. As another example, the high-voltage device may be stationary while the one or more imaging radiation sources rotate.

In some embodiments, the imaging assembly may be configured to perform a multi-energy imaging of the object. For example, at least two imaging beams from at least two of the one or more imaging radiation sources have different energy levels, and an image of the object may be generated based on an imaging dataset corresponding to each of the at least two imaging beams detected by one of the one or more detectors. A multi-energy image may be generated by fusing at least two images generated based on at least two imaging datasets corresponding to the at least two imaging beams. As another example, one of the one or more imaging radiation sources may emit different imaging beams of different energy levels, and an image of the object may be generated based on an imaging dataset corresponding to each of the different imaging beams of different energy levels detected by one of the one or more detectors. A multi-energy image may be generated by fusing different images generated based on imaging datasets corresponding to the different imaging beams of different energy levels. The imaging radiation source may emit the different imaging beams of different energy levels by adjusting a voltage of the imaging radiation source. As a further example, at least one (e.g., a layer detector) of the one or more detectors may divide an imaging beam (that is detected) into different portions of different energy levels, each portion of which is of a same energy level, and further generate an image based on an image dataset generated based on each of the different portions of the detected imaging beam. A multi-energy image may be generated by fusing different images generated based on imaging datasets corresponding to the different portions of the detected imaging beam.

In the present disclosure, the x axis, they axis, and the z axis shown in FIG. 1 may form an orthogonal coordinate system. The x axis and the y axis shown in FIG. 1 may be horizontal, and the z axis may be vertical. As illustrated, the positive x direction along the x axis may be from the right side to the left side of the radiation device 110 seen from the direction facing the front of the radiation device 110; the positive z direction along the z axis shown in FIG. 1 may be from the lower part to the upper part of the radiation device 110; the positive y direction along the y axis shown in FIG. 1 may refer to a direction in which an object is moved out of a bore of the radiation device 110.

In some embodiments, the radiation device 110 may also include a gantry 111 and a patient support 113. In some embodiments, the gantry 111 may be configured to support at least one of the treatment head 112, the one or more imaging radiation sources, the one or more detectors, the first assistance assembly, or the second assistance assembly. In some embodiments, the gantry 111, or a portion thereof (e.g., the first gantry portion as described elsewhere in the present disclosure), may be configured to rotate around an object (e.g., a patient) that is moved into a field of view (FOV) (e.g., a region covered by one or more radiation beams emitted from at least one of the treatment head 112 or the one or more imaging radiation sources) of the radiation device 110. In some embodiments, the patient support 113 may be configured to support the object. In some embodiments, the patient support 113 may have 6 degrees of freedom, for example, three translational degrees of freedom along three coordinate directions (i.e., x direction, y direction, and z direction illustrated in FIG. 1) and three rotational degrees of freedom around the three coordinate directions. Accordingly, the patient support 113 may move the object along any direction of the 3D coordinate system illustrated in FIG. 1. Merely by way of example, the patient support 113 may move the object into the FOV of the radiation device 110 along they direction in FIG. 1.

In some embodiments, the gantry 111 may have a rotation axis parallel to they direction in FIG. 1. In some embodiments, the gantry 111 may include a C-arm gantry. For example, the treatment head 112 may be mounted on the C-arm gantry in a cantilever-like manner. In some embodiments, the gantry 111 may include a ring gantry (e.g., as shown in FIG. 1) having a toroidal shape in which the patient's body extends through a bore (e.g., the bore 211 in FIG. 2) of the ring. For example, at least one of the treatment head 112, the one or more imaging radiation sources, and the one or more detectors may be mounted on the perimeter of the ring gantry. In some embodiments, the gantry 111 may be configured to rotate in a direction (e.g., the clockwise direction or the anticlockwise direction). In some embodiments, the gantry 111 may be configured to rotate and reverse repeatedly.

In some embodiments, the treatment head 112 may be configured to be operably coupled to or mounted on the gantry 111. The treatment head 112 may rotate about the rotation axis and within a rotation plane (or referred to as a rotation ring or simply a ring). A center point of the rotation plane may be referred to as an isocenter (e.g., an isocenter 416 in FIG. 4) of the treatment assembly. The rotation axis may pass through the isocenter and be perpendicular to the rotation plane.

In some embodiments, at least one of the one or more imaging radiation sources or the one or more detectors may be operably coupled to or mounted on, or separated from the gantry 111. In some embodiments, at least one of the one or more imaging radiation sources and the one or more detectors may move with or independently of the gantry 111. In some embodiments, at least one of the one or more imaging radiation sources or the one or more detectors may be operably coupled to or mounted on a rotation ring (e.g., a second ring 902 in FIG. 9B) other than the gantry 111. The at least one of the one or more imaging radiation sources or the one or more detectors may move with the rotation ring. The rotation ring may be operably coupled to, mounted on, or separated from the gantry 111. The rotation ring may move with or independently of the gantry 111. In some embodiments, the one or more detectors or the one or more imaging radiation sources may be static or substantially static relative to each other. As used herein, two devices, e.g., two imaging radiation sources, an imaging radiation source and a detector (e.g., a first detector, a second detector) being static to each other indicates that the relative positioning of the two devices stay unchanged regardless of whether at least one of the two devices moves with respect to the gantry 111 or the patient support 113.

In some embodiments, the one or more imaging radiation sources and the one or more detectors may rotate about the rotation axis of the gantry 111 and within a rotation plane (or referred to as a rotation ring or simply a ring). A center point of the rotation plane may be referred to as an isocenter of the imaging assembly. The rotation axis may pass through the isocenter and be perpendicular to the rotation plane.

In some embodiments, the rotation trajectories of the treatment head 112, at least one of the one or more imaging radiation sources, and at least one of the one or more detectors may be located along a same circle or different circles. In some embodiments, the treatment head 112, at least one of the one or more imaging radiation sources, and at least one of the one or more detectors may rotate in a same plane or different planes. Details regarding the radiation device 110 can be found elsewhere in the present disclosure (e.g., descriptions in connection with FIGS. 2-9B).

In some embodiments, the object may be biological or non-biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof. In the present disclosure, "subject" and "object" are used interchangeably.

The network 150 may facilitate exchange of information and/or data. In some embodiments, one or more components of the radiation system 100 (e.g., the radiation device 110, the processing device 120, the storage device 130, or the terminal 140) may send information and/or data to another component(s) in the radiation system 100 via the network 150. For example, the processing device 120 may obtain a user instruction from the terminal 140 via the network 150. As another example, the processing device 120 may obtain scan data (e.g., projection data) from the radiation device 110 via the network 150. In some embodiments, the network 150 may be any type of wired or wireless network, or combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired or wireless network access points such as base stations and/or internet exchange points through which one or more components of the radiation system 100 may be connected to the network 150 to exchange data and/or information.

The terminal 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 140 may remotely operate the radiation device 110. In some embodiments, the terminal 140 may operate the radiation device 110 via a wireless connection. In some embodiments, the terminal 140 may receive information and/or instructions inputted by a user, and send the received information and/or instructions to the radiation device 110 or to the processing device 120 via the network 150. In some embodiments, the terminal 140 may receive data and/or information from the processing device 120. In some embodiments, the terminal 140 may be part of the processing device 120. In some embodiments, the terminal 140 may be omitted.

In some embodiments, the processing device 120 may process data obtained from the radiation device 110, the storage device 130, or the terminal 140. For example, the processing device 120 may obtain projection data of an object from the radiation device 110 and generate an image of the object based on the projection data. As another example, the processing device 120 may cause one or more components (e.g., a treatment head, an imaging radiation source, a detector, a collimator, a patient support, a gantry, etc.) of the radiation device 110 to be located at a specific position. The processing device 120 may be a central processing unit (CPU), a digital signal processor (DSP), a system on a chip (SoC), a microcontroller unit (MCU), or the like, or any combination thereof.

In some embodiments, the processing device 120 may be a single server or a server group. The server group may be centralized or distributed. In some embodiments, the processing device 120 may be local or remote. For example, the processing device 120 may access information and/or data stored in the radiation device 110, the storage device 130, and/or the terminal 140 via the network 150. As another example, the processing device 120 may be directly connected to the radiation device 110, the storage device 130, and/or the terminal 140, to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data and/or instructions. In some embodiments, the storage device 130 may store data obtained from the terminal 140 and/or the processing device 120. For example, the storage device 130 may store one or more images generated by the processing device 120. In some embodiments, the storage device 130 may store data and/or instructions that the processing device 120 may execute or use to perform exemplary methods described in the present disclosure. For example, the storage device 130 may store instructions that the processing device 120 may execute or use to generate one or more images based on projection data. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more components of the radiation system 100 (e.g., the radiation device 110, the processing device 120, the terminal 140). One or more components of the radiation system 100 may access the data or instructions stored in the storage device 130 via the network 150. In some embodiments, the storage device 130 may be directly connected to or communicate with one or more components of the radiation system 100 (e.g., the processing device 120, the terminal 140). In some embodiments, the storage device 130 may be part of the processing device 120.

Figure 2:
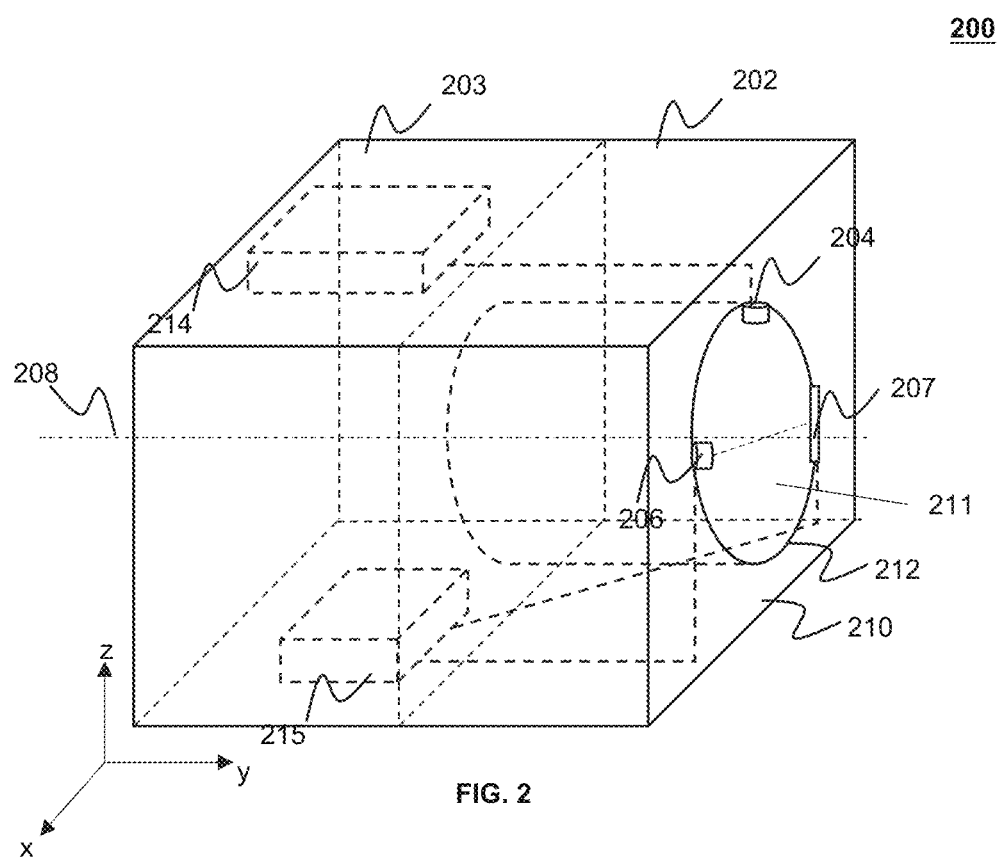
FIGS. 2-9B are schematic diagrams illustrating exemplary configurations of a radiation device according to some embodiments of the present disclosure.
Figure 3:
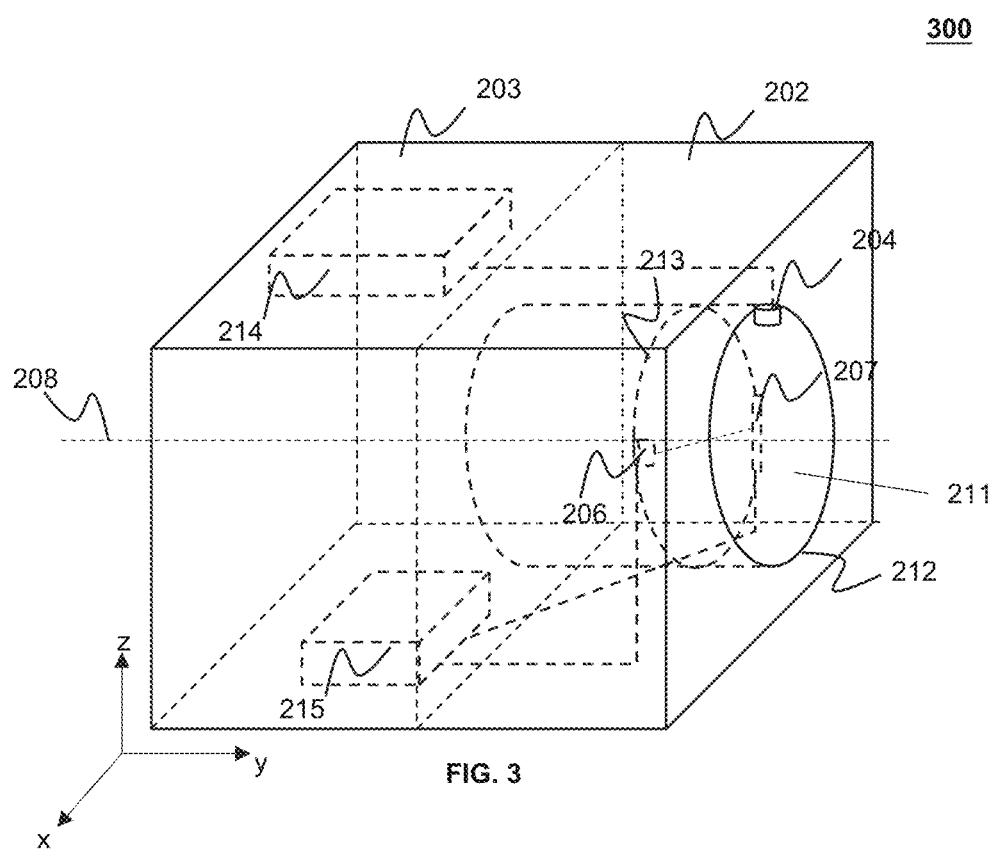

FIG. 2 and FIG. 3 are schematic diagrams illustrating exemplary configurations of the radiation device 110 according to some embodiments of the present disclosure.

According to the configuration 200 or 300 shown in FIG. 2 and FIG. 3, the radiation device 110 may include a treatment assembly, an imaging assembly, and a gantry 210. The treatment assembly may include a treatment head 204 and a first assistance assembly 214. The imaging assembly may include a first imaging radiation source 206 (e.g., a CT imaging radiation source), a first detector 207 (e.g., a CT detector), and a second assistance assembly 215. As shown in FIG. 2 and FIG. 3, the gantry 210 may include a first gantry portion 202 and a second gantry portion 203 located next to the first gantry portion 202 along a rotation axis 208 of the radiation device 110 (or the gantry 210). As used herein, the first gantry portion 202 and the second gantry portion 203 being located next to each other indicates that there are no other rotation rings between the first gantry portion 202 and the second gantry portion 203.

In some embodiments, the first gantry portion 202 and the second gantry portion 203 may be accommodated in a housing of the gantry 210. In some embodiments, the first gantry portion 202 and the second gantry portion 203 may be accommodated in different housings inside the gantry 210, respectively. For instance, the first gantry portion 202 and the second gantry portion 203 may be accommodated in different housings that are stationary relative to each other. As another example, the first gantry portion 202 and the second gantry portion 203 may be accommodated in different housings that may move relative to each other (e.g., the housing accommodating the first gantry portion 202 being configured to rotate, while the housing accommodating the second gantry portion 203 being stationary).

In some embodiments, the first gantry portion 202 and the second gantry portion 203 may be integrated as a whole gantry (e.g., the gantry 210) and rotate together. In some embodiments, the first gantry portion 202 and the second gantry portion 203 may be integrated as a whole gantry (e.g., the gantry 210), and the first gantry portion 202 may rotate independently from the second gantry portion 203. In some embodiments, the first gantry portion 202 and the second gantry portion 203 may be two independent portions of the gantry 210 that rotate synchronously. In some embodiments, the first gantry portion 202 and the second gantry portion 203 may be two independent portions of the gantry 210 and the first gantry portion 202 may rotate independently from the second gantry portion 203.

In some embodiments, the treatment head 204, the first imaging radiation source 206, and the first detector 207 may be disposed on the first gantry portion 202. In some embodiments, the first gantry portion 202 may have a rotation axis. In some embodiments, the first gantry portion 202 may rotate about the rotation axis. In some embodiments, the rotation axis of the first gantry portion 202 may coincide with the rotation axis of the gantry 210 or the rotation axis 208 of the radiation device 110 as described elsewhere in the present disclosure. Merely by way of example, the first imaging radiation source 206 and the first detector 207 may be disposed in a first section of the first gantry portion 202. The treatment head 204 may be disposed in a second section of the first gantry portion 202. In some embodiments, the first section may be configured to rotate independently from the second section. The first section may be configured to rotate in a first range without collision with the second section. In some embodiments, the treatment head may be configured to move radially away from a rotation axis of the gantry 210 to allow the first section to rotate independently in a second range without collision. As used herein, the second range may be larger than the first range. The rotation axis of the gantry 210 may coincide with the rotation axis 208 of the radiation device 110 as described elsewhere in the present disclosure.

In some embodiments, the first section and the second section may be arranged in parallel along the rotation axis 208 of the radiation device 110. See, e.g., FIG. 4 and the description thereof. In some embodiments, the first section and the second section may be concentrically arranged. See, e.g., FIG. 5 and the description thereof. In some embodiments, at least part of the second gantry portion 203 may rotate along with the treatment head 204 or the first imaging radiation source 206. In some embodiments, at least part of the second gantry portion 203 may be stationary while the treatment head 204 or the first imaging radiation source 206 rotates.

In some embodiments, the first assistance assembly 214 and the second assistance assembly 215 may be housed within the second gantry portion 203. Merely by way of example, the first assistance assembly 214 may be located at a portion of the second gantry portion 203 different from the second assistance assembly 215 shown in FIG. 2 and FIG. 3. It should be noted that the above descriptions are for illustration purposes and non-limiting. As described in connection with FIG. 1, the first assistance assembly 214 or the second assistance assembly 215 may include different components. In some embodiments, the components of the first assistance assembly 214 or the second assistance assembly 215 may be separately arranged in the space available in the second gantry portion 203 according to practical demands. For example, different components of the first assistance assembly 214 may be located at different portions of the second gantry portion 203. As another example, different components of the second assistance assembly 215 may be located at different portions of the second gantry portion 203. As a further example, different components of the first assistance assembly 214 may be clustered and disposed at one portion of the second gantry portion 203, while different components of the second assistance assembly 215 may be clustered and disposed at another portion of the second gantry portion 203 as illustrated in FIGS. 2 and 3.

In some embodiments, the treatment head 204, the first imaging radiation source 206, and the first detector 207 may be configured to rotate in a same rotation plane; that is, the first imaging radiation source 206 and the first detector 207 may rotate along with the treatment head 204. For example, the treatment head 204, the first imaging radiation source 206, and the first detector 207 may be configured to rotate in a same rotation plane, e.g., a first rotation plane 212, perpendicular to the rotation axis 208 of the radiation device 110 in FIG. 2.

In some embodiments, the treatment head 204, the first imaging radiation source 206, and the first detector 207 may be rotated in different rotation planes. As shown in FIG. 3, the treatment head 204 may be configured to rotate in a first rotation plane 212 perpendicular to the rotation axis 208 of the radiation device 110. The first imaging radiation source 206 and the first detector 207 may be configured to rotate in a second rotation plane 213 that is perpendicular to the rotation axis 208 of the radiation device 110 and different from the first rotation plane 212. In some embodiments, the second rotation plane 213 may be closer to the second gantry portion than the first rotation plane 212; that is, the first imaging radiation source 206 and the first detector 207 may be located between the second gantry portion 203 and the treatment head 204.

As shown in FIG. 2 and FIG. 3, a bore 211 of the gantry 210 may extend within the first gantry portion 202, which is for illustration purposes and non-limiting. In some embodiments, the bore 211 of the gantry 210 may extend from the first gantry portion 202 to at least a portion of the second gantry portion 203. For example, the bore 211 of the gantry 210 may extend through the first gantry portion 202 and the second gantry portion 203. As another example, the bore 211 of the gantry 210 may extend from the first gantry portion 202 through at least a portion of the second gantry portion 203.

In some embodiments, a treatment head (e.g., the treatment head 112 in FIG. 1, the treatment head 204 in FIG. 2) of the radiation device 110 may include a primary collimator configured to define a maximum treatment radiation region. A treatment beam emitted by the treatment head may travel within the maximum treatment radiation region from the treatment head toward the object. In some embodiments, the treatment head may include a secondary collimator (e.g., a collimator 602 in FIG. 6). The secondary collimator may be located below the primary collimator and positioned relative to the treatment head. As used herein, component A being below component B indicates that component B is closer to a treatment radiation source (e.g., a treatment radiation source 610) than component A. The secondary collimator may configure a size, location, and/or shape of the treatment beam within the maximum treatment radiation region to make the collimated treatment beam approximate and target at a target volume inside the object. In some embodiments, the secondary collimator may be positioned on a treatment beam pathway of the treatment beam. In some embodiments, the secondary collimator may include a multi-leaf collimator (MLC).

Figure 4:
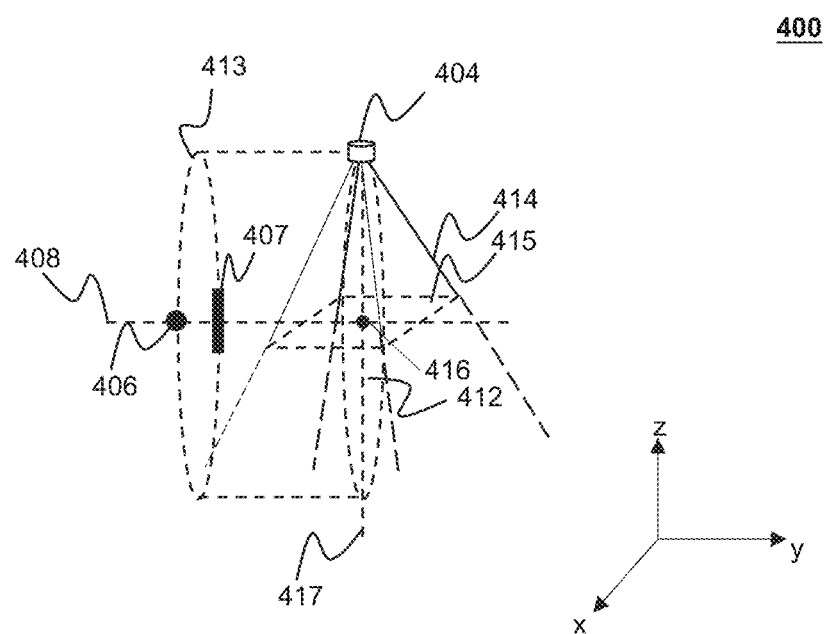

A plane perpendicular to the central axis (e.g., 417 in FIG. 4) of the treatment beam and passing through the isocenter (e.g., 416 in FIG. 4) of the treatment assembly may be referred to as an isocenter plane (e.g., 415 in FIG. 4). The maximum treatment radiation region may provide a maximum treatment field (e.g., 608 in FIG. 6) on the isocenter plane.

As shown in FIG. 4, the region of the maximum treatment radiation region above the isocenter plane 415 may be referred to as a first treatment sub-region, and the region of the maximum treatment radiation region below the isocenter plane 415 may be referred to as a second treatment sub-region. In some embodiments, the first treatment sub-region and the second treatment sub-region may constitute the maximum treatment radiation region of the treatment beam. As shown in FIG. 4, the region proximal to the isocenter plane 415 along an emitting direction of the treatment beam and delineated by the solid lines indicating the treatment beam 414 may be referred to as a first treatment sub-region. The region distal to the isocenter plane 415 along the emitting direction of the treatment beam and delineated by the dashed lines indicating the treatment beam 414 may be referred to as a second treatment sub-region.

When the treatment head is delivering a treatment beam to an object (e.g., a patient), if there is a foreign matter (e.g., the one or more imaging radiation sources, the one or more detectors) within the first treatment sub-region, the foreign matter may obstruct at least a portion of the treatment beam from reaching the object, thereby affecting the radiation treatment and/or the imaging of the object. In addition, the exposure of a device, e.g., any one of the one or more imaging radiation sources, the one or more detectors, to the treatment beam may cause damage to the device, which in turn may reduce the lifetime of the device.

In some embodiments, when the treatment head is delivering the treatment beam to the object, the one or more imaging radiation sources and the one or more detectors may be positioned outside the first treatment sub-region so that the one or more imaging radiation sources, the one or more detectors may perform imaging without interfering with the treatment beam. In this context, at least one of the one or more imaging radiation sources, the one or more detectors may be positioned in a close proximity to the first treatment sub-region. For example, at least one of the one or more imaging radiation sources, the one or more detectors may be positioned at or near an edge of the first treatment sub-region.

When the treatment beam is also used to imaging the object, if there is a foreign matter within the second treatment sub-region, the foreign matter may obstruct at least a portion of the treatment beam from reaching a treatment beam detector configured to detect at least a portion of the treatment beam, thereby affecting the imaging of the object. In some embodiments, the one or more imaging radiation sources and the one or more imaging beam detectors configured to detect imaging beam(s) (except the treatment beam detector) may be removed from the pathway of the treatment beam. For instance, when the treatment head is delivering the treatment beam to an object, the one or more imaging radiation sources and the one or more imaging beam detectors may be positioned outside the treatment region (not only the first treatment sub-region but also the second treatment sub-region) so that the one or more imaging radiation sources and the one or more imaging beam detectors may perform imaging without interfering with the treatment beam, and/or the exposure of the one or more imaging radiation sources and the one or more imaging beam detectors may be avoided. In this context, at least one of the one or more imaging radiation sources and the one or more imaging beam detectors may be positioned in a close proximity to the treatment region. For example, at least one of the one or more imaging radiation sources and the one or more imaging beam detectors may be positioned within or outside the treatment region at or near an edge of the treatment region.

In some embodiments, the treatment beam may be collimated to a collimated treatment beam. The collimated treatment beam may provide a collimated treatment radiation region that is smaller than the maximum treatment radiation region of the treatment beam. The collimated treatment radiation beam may provide a target-specific treatment area on the isocenter plane of the treatment assembly. The target-specific treatment area may be smaller than the maximum treatment field of the maximum radiation treatment region. The intersection of the maximum treatment radiation region with the target-specific treatment area may constitute the collimated treatment radiation region. A portion of the collimated treatment radiation region proximal to the isocenter plane along an emitting direction of the treatment beam may be referred to as a third treatment sub-region. A portion of the collimated treatment radiation region distal to the isocenter plane along the emitting direction of the treatment beam may be referred to as a fourth treatment sub-region.

For instance, when the treatment head is delivering the treatment beam to an object, the one or more imaging radiation sources and the one or more detectors may be positioned outside the third treatment sub-region so that the one or more imaging radiation sources and the one or more detectors do not interfere with the collimated treatment beam. In this context, at least one of the one or more imaging radiation sources and the one or more detectors may be positioned in a close proximity to the third treatment sub-region. For example, at least one of the one or more imaging radiation sources and the one or more detectors may be positioned at an edge of the third treatment sub-region of the collimated treatment beam, other than the first treatment sub-region of the treatment beam, which indicates that the at least one of the one or more imaging radiation sources and the one or more detectors may be positioned "near" the edge of the first treatment sub-region. In this way, a projection, along the treatment beam onto the isocenter plane of the treatment assembly, of the at least one of the one or more imaging radiation sources and the one or more detectors may be within the maximum treatment field of the treatment head.

In some embodiments, if the treatment beam is also used to imaging the object, when the treatment head is delivering the treatment beam to the object, the one or more imaging radiation sources and the one or more imaging beam detectors may be positioned outside the collimated treatment radiation region so that the one or more imaging radiation sources and the one or more imaging beam detectors may perform imaging without interfering with the collimated treatment beam. In this context, at least one of the one or more imaging radiation sources and the one or more imaging beam detectors may be positioned in a close proximity to the collimated treatment radiation region. For example, at least one of the one or more imaging radiation sources and the one or more imaging beam detectors may be positioned at an edge of the collimated treatment radiation region, other than the treatment region of the treatment beam, which indicates that the at least one of the one or more imaging radiation sources and the one or more imaging beam detectors may be positioned "near" the edge of the treatment region of the treatment beam. In this way, a projection, along the treatment beam onto the isocenter plane, of the at least one of the one or more imaging radiation sources and the one or more imaging beam detectors may be within the maximum treatment field of the treatment head.

Figure 6:
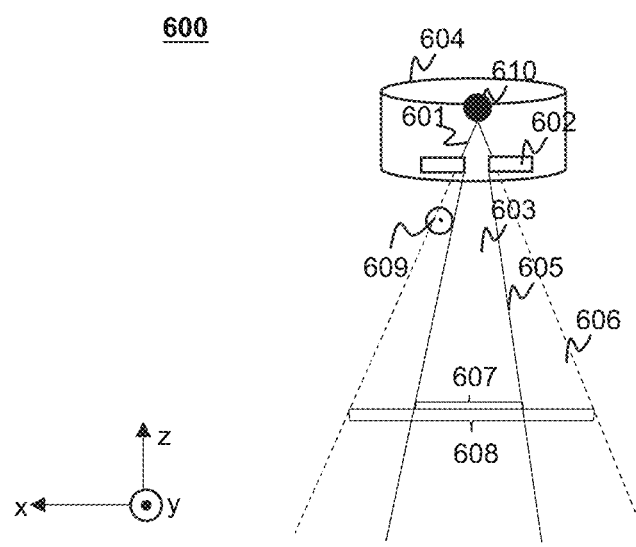

FIG. 6 is a schematic diagram illustrating a cross-section of an exemplary configuration 600 of the radiation device 110 according to some embodiments of the present disclosure. The configuration 600 of the radiation device 110 shown in FIG. 6 is a view of the radiation device 110 from the direction facing the front of the radiation device 110 (e.g., along the negative y direction in FIG. 1). The x, y, and z directions in FIG. 6 may correspond to those in FIG. 1. In FIG. 6, the positive y direction is vertical to the paper and points outward.

As shown in FIG. 6, a treatment radiation source 610 (e.g., an X-ray target) of a treatment head 604 may emit a treatment beam 601 that provides a first treatment region 606 with a maximum treatment field 608 (e.g., 40 cm×40 cm). The treatment beam 601 may be collimated by a collimator 602 (e.g., a secondary collimator) to a collimated treatment beam 605. The collimated treatment beam 605 may provide a second treatment region 603 smaller than the first treatment region 606. The collimated treatment beam 605 may provide a target-specific treatment area 607 (e.g., 15 cm×15 cm) that is smaller than the maximum treatment field 608.

As shown in FIG. 6, when the treatment head 604 is delivering the treatment beam 601 to an object, an imaging radiation source 609 may be positioned at an edge of the second treatment region 603, which indicates that the imaging radiation source 609 is positioned near an edge of the first treatment region 606. A projection, along the treatment beam 601 onto the isocenter plane of the treatment assembly, of the imaging radiation source 609 may be within the maximum treatment field 608.

In some embodiments, a treatment assembly of the radiation device 110 may include a treatment head, and an imaging assembly of the radiation device 110 may include a first imaging radiation source (e.g., a CT imaging radiation source), and a first detector corresponding to the first imaging radiation source. The first imaging radiation source may be located as close as possible to the treatment head without interference with a treatment beam emitted by the treatment head. In some embodiments, there may be an angular offset between the first imaging radiation source and the treatment head. For example, when the treatment head is delivering the treatment beam to an object along a first direction, the first imaging radiation source may be positioned so that the first imaging radiation source delivers the imaging beam along a second direction. A difference between the first direction and the second direction may be below 30 degrees so that the imaging beam is in a close vicinity to the orientation of the treatment beam. The first direction may be the direction of the center axis of the treatment beam. The second direction may be the direction of the center axis of the imaging beam of the first imaging radiation source. In this way, more projection data substantially along or close to the first direction may be acquired, thereby facilitating the detection of anatomy and/or motion (which for photon treatments is the most problematic type of motion) of the ROI (including, e.g., the target volume, an OAR, etc.) of the object perpendicular to the treatment beam (e.g., the first direction).

In some embodiments, the treatment head, the first imaging radiation source and the first detector may be configured to rotate in different rotation planes. In such cases, the first imaging radiation source may be positioned apart from the treatment head by a certain distance along the rotation axis of the radiation device 110. The distance may be below a threshold (e.g., 20 centimeters, 40 centimeters, 50 centimeters, 80 centimeters, 1 meter). An isocenter of the treatment assembly may be within the rotation plane of the treatment head. An isocenter of the imaging assembly may be within the rotation plane of the first imaging radiation source. Accordingly, the distance between the isocenter of the treatment assembly and the isocenter of the imaging assembly along the rotation axis may be below the threshold (e.g., 20 centimeters, 40 centimeters, 50 centimeters, 80 centimeters, 1 meter).

FIG. 4 is a schematic diagram illustrating an exemplary configuration 400 of the radiation device 110 according to some embodiments of the present disclosure. According to the configuration 400, a treatment head 404, a first imaging radiation source 406, and a first detector 407 may be configured to rotate in different rotation planes about a rotation axis 408 of the radiation device 110. For example, the treatment head 404 may rotate in a first rotation plane 412 and the first imaging radiation source 406 and the first detector 407 may rotate in a second rotation plane 413 different from the first rotation plane 412. The second rotation plane 413 may be located at an edge of a treatment beam 414 emitted by the treatment head 404.

As shown in FIG. 4, there may be a distance between the first rotation plane 412 and the second rotation plane 413, that is, the first imaging radiation source may be positioned apart from the treatment head by a certain distance along the rotation axis 408 of the radiation device 110, in which the distance may be below a threshold (e.g., 20 centimeters, 40 centimeters, 50 centimeters, 80 centimeters, 1 meter). An isocenter of the treatment assembly may be at the intersection of the rotation axis 408 and the rotation plane 412. An isocenter of the imaging assembly may be at the intersection of the rotation axis 408 and the rotation plane 413. Accordingly, the distance between the isocenter of the treatment assembly (or the first rotation plane 412) and the isocenter of the imaging assembly (or the second rotation plane 413) may be below the threshold (e.g., 20 centimeters, 40 centimeters, 50 centimeters, 80 centimeters, 1 meter).

Figure 5:
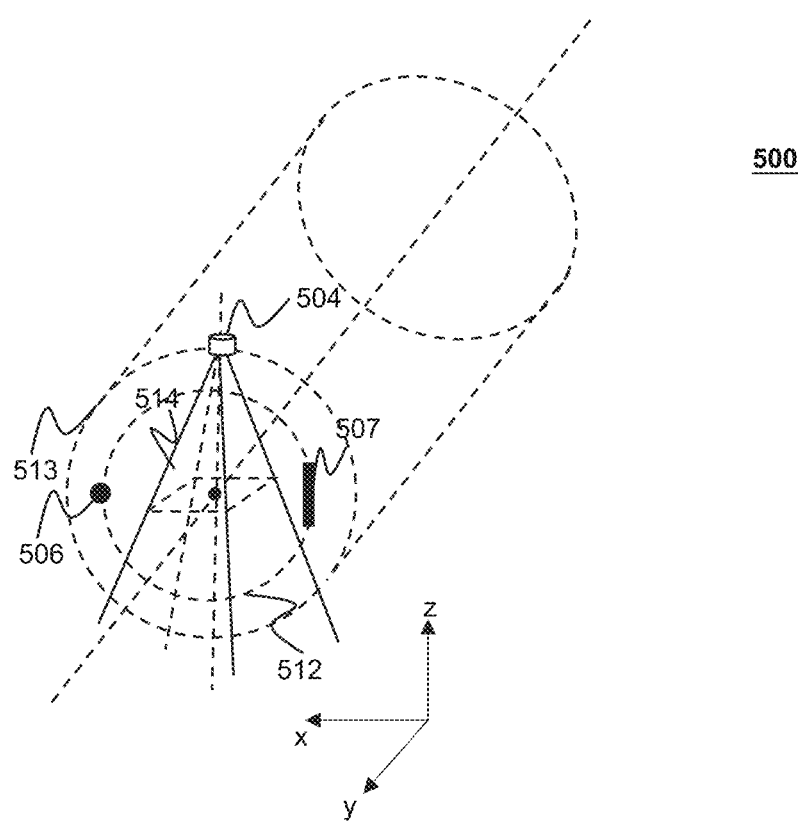

For example, FIG. 5 is a schematic diagram illustrating an exemplary configuration 500 of the radiation device 110 according to some embodiments of the present disclosure. According to the configuration 500, a treatment head 504, a first imaging radiation source 506, and a first detector 507 may be rotated in a same rotation plane. The first imaging radiation source 506 and the first detector 507 may be located on a first ring 512. The treatment head 504 may be located on a second ring 513 different from the first ring 512. The first ring 512 and the second ring 513 may be concentric.

In some embodiments, the first imaging radiation source 506 and the first detector 507 may be configured to oscillate so as not to interfere with a first treatment sub-region of a treatment beam 514. The treatment beam 514 may form the maximum treatment field of the treatment head 504. For example, when the treatment beam 514 is on, the first ring 512 carrying the first imaging radiation source 506 and the first detector 507 may be positioned such that the first imaging radiation source 506 and the first detector 507 are positioned outside the first treatment sub-region; when the treatment beam 514 is off, the first ring 512 carrying the first imaging radiation source 506 and the first detector 507 may move such that at least a portion of the first imaging radiation source 506 is positioned in the first treatment sub-region and at least a portion of the first detector 507 is positioned within the second treatment sub-region; when the treatment beam 514 is resumed, the first ring 512 carrying the first imaging radiation source 506 and the first detector 507 may move such that the first imaging radiation source 506 and the first detector 507 are positioned outside the first treatment sub-region again. In some embodiments, by the oscillatory movement, at least one of the first imaging radiation source 506 or the first detector 507 is moved into and out of the first treatment sub-region. In some embodiments, by the oscillatory movement, at least one of the first imaging radiation source 506 or the first detector 507 is moved into and out of the second treatment sub-region. In this way, the imaging beam may be substantially along or close to the treatment beam's eye view; that is, the imaging beam may be substantially along or close to a first direction of the central axis of the treatment beam 514. The imaging data so acquired may better delineate the anatomy and/or motion of the ROI (including, e.g., the target volume, an OAR, etc.) of the object that the treatment beam (e.g., the first direction) encounters.

In some embodiments, the delivery of the treatment beam and the delivery of the first imaging beam may alternate. For example, the first imaging radiation source may be configured to emit the first imaging beam when a delivery of the treatment beam to the object is paused. In such cases, the first gantry portion of the gantry may rotate at a first speed when the first imaging beam is delivered and rotate at a second speed when the treatment beam is delivered. In some embodiments, the first speed may be faster than the second speed.

In some embodiments, the delivery of the treatment beam and the delivery of the first imaging beam may be concurrent. For example, the first imaging radiation source may be configured to emit the first imaging beam while the treatment head is delivering the treatment beam to the object. In such cases, the first gantry portion may rotate at a third speed when the first imaging beam and the treatment beam are delivered, that is, the first imaging radiation source, the first detector, and the treatment head rotate at the third speed. In some embodiments, the third speed may be the same as or different from the first speed or the second speed.

In some embodiments, a first angular projection range of the first imaging radiation source may be a portion of a full angular projection range of the radiation system. The first imaging radiation source may be configured to rotate, while the treatment head is delivering the treatment beam to the object or when a delivery of the treatment beam to the object is paused, to cover a second angular projection range. The first angular projection range and the second angular projection range may constitute the full angular projection range of the radiation device 110.

In some embodiments, the first imaging radiation source and the first detector may be configured to move in a range of 360 degrees without collision with other components (e.g., the treatment head) of the radiation device 110. In some embodiments, the first imaging radiation source and the first detector may be configured to move in a limited angle range less than 360 degrees. The treatment head may be configured to move radially away from an isocenter of the radiation system (e.g., the isocenter of the treatment assembly) to allow movement of the first imaging radiation source and the first detector in a range of 360 degrees.

For example, the first imaging radiation source and the first detector may be positioned to move along a same rotation ring. The first imaging radiation source and the first detector may be able to move independently in a limited angle range less than 360 degrees. By the radial movement of the treatment head, the treatment head may make room for independent movement of the first imaging radiation source and the first detector.

In some embodiments, the first imaging radiation source may be configured to move, along with the first detector, around the rotation axis of the gantry and independently of the gantry in a first range less than or equal to 360 degrees without collision. In some embodiments, the treatment head may be configured to move (e.g., move radially away from the isocenter of the imaging assembly, or move along the y direction) to make room for the independent movement of the first imaging radiation source and the first detector, thereby allowing the independent movement of the first imaging radiation source and the first detector in a second range without collision. The second range may be larger than the first range.

In some embodiments, the first imaging radiation source may be configured to perform a one-directional rotation (e.g., a clockwise rotation or an anti-clockwise rotation) within a range of 360 degrees for one time or repeatedly. Accordingly, the first imaging radiation source may rotate within any angular range (e.g., 45 degrees, 90 degrees, 180 degrees, 270 degrees, 360 degrees, 720 degrees). For example, the first imaging radiation source may rotate along a direction for only one rotation. As another example, the first imaging radiation source may rotate along a direction for a plurality of rotations. In some embodiments, the first imaging radiation source may be configured to perform an oscillation in a range of 360 degrees or a limited angle range less than 360 degrees. As used herein, an oscillation refers to moving forward and backward, e.g., along the clockwise direction and then the anti-clockwise direction, or vice versa.

Figure 9A:
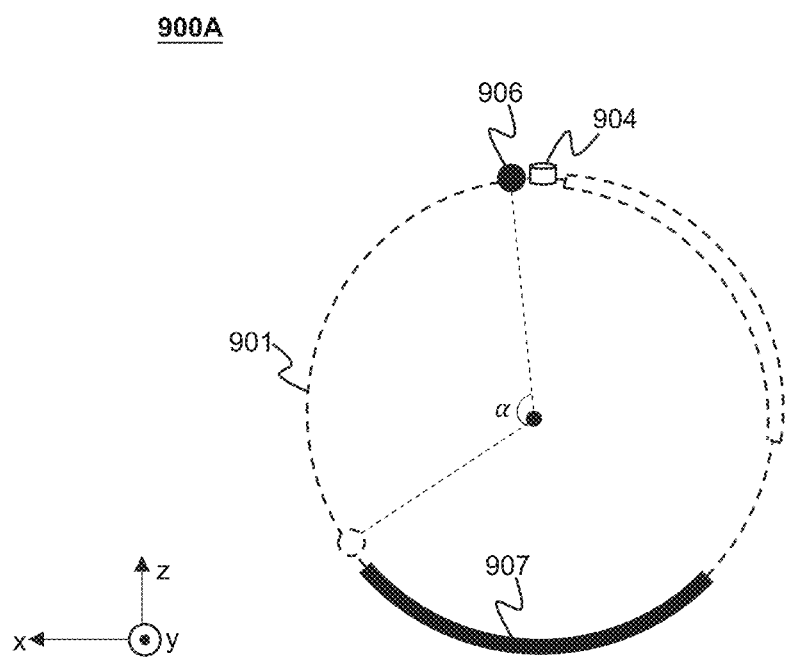

FIG. 9A is a schematic diagram illustrating a cross-section of an exemplary configuration 900A of the radiation device 110 according to some embodiments of the present disclosure. The configuration 900A of the radiation device 110 shown in FIG. 9A is a view of the radiation device 110 from the direction facing the front of the radiation device 110 (e.g., along the negative y direction in FIG. 1). The x, y, and z directions in FIG. 9A may correspond to those in FIG. 6.

As shown in FIG. 9A, according to the configuration 900A, the radiation device 110 may include a treatment head 904, a first imaging radiation source 906, a first detector 907 (e.g., a curvilinear detector) mounted on a ring 901. The first imaging radiation source 906 and the first detector 907 may rotate independently of the treatment head 904 in an angular range a. The first imaging radiation source 906 and the first detector 907 may be configured to rotate within the angular range a independently so as not to interfere with the first treatment sub-region of the treatment beam with the maximum treatment field. For example, when the treatment beam is on, the first imaging radiation source 906 and the first detector 907 may be rotated such that the first imaging radiation source 906 and the first detector 907 are positioned outside the first treatment sub-region; when the treatment beam is off, the first imaging radiation source 906 and the first detector 907 may rotate such that at least a portion of the first imaging radiation source 906 is positioned in the first treatment sub-region and at least a portion of the first detector 907 is positioned inside the second treatment sub-region; when the treatment beam is resumed, the first imaging radiation source 906 and the first detector 907 are positioned such that the first imaging radiation source 906 and the first detector 907 are positioned outside the first treatment sub-region again.

Figure 9B:
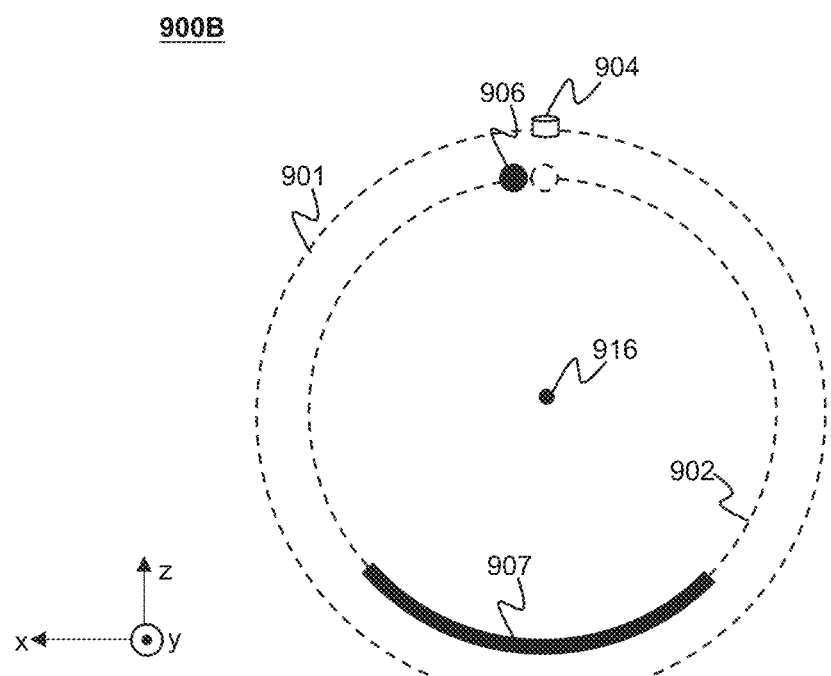

FIG. 9B is a schematic diagram illustrating a cross-section of an exemplary configuration 900B of the radiation device 110 according to some embodiments of the present disclosure. The configuration 900B of the radiation device 110 shown in FIG. 9B is a view of the radiation device 110 from the direction facing the front of the radiation device 110 (e.g., along the negative y direction in FIG. 1). The x, y, and z directions in FIG. 9B may correspond to those in FIG. 6, respectively.

As shown in FIG. 9B, according to the configuration 900B, the radiation device 110 may include a treatment head 904 mounted on a first ring 901 and a first imaging radiation source 906 and a first detector 907 (e.g., a curvilinear detector) mounted on a second ring 902. The first imaging radiation source 906 and the first detector 907 may rotate independently of the treatment head 904. In some embodiments, the treatment head may be configured to move radially away from an isocenter 916 of the radiation device 110 to allow the first imaging radiation source and the first detector to rotate independently in a range (360 degrees) without collision.

In some embodiments, the radiation device 110 may include a treatment head, a first imaging radiation source (e.g., the first imaging radiation source illustrated in FIGS. 1-6, 9A, and 9B), at least one second imaging radiation source (e.g., the at least one second imaging radiation source illustrated in FIG. 1), a first detector corresponding to the first imaging radiation source (e.g., the first detector illustrated in FIGS. 1-6, 9A, and 9B), and at least one second detector corresponding to the at least one second imaging radiation source (e.g., the at least one second detector illustrated in FIG. 1). As used herein, the first imaging radiation source and the at least one second imaging radiation source may be collectively referred to as "one or more imaging radiation sources." The first detector and the at least one second detector may be collectively referred to as "one or more detectors."

In some embodiments, at least two of the one or more imaging radiation sources may share one of the one or more detectors. The shared detector may be configured to detect at least two imaging beams, each from a different imaging radiation source of the at least two imaging radiation sources. For example, the first imaging radiation source and one of the at least one second imaging radiation source may share the first detector. As another example, two of the at least one second imaging radiation source may share one of the at least one second detector. In some embodiments, each of the one or more imaging radiation sources may correspond to one of the one or more detectors.

In some embodiments, at least one of the one or more imaging radiation sources (or the at least one second imaging radiation source) and the treatment head may be configured to rotate in a same rotation plane (e.g., the rotation plane of the treatment head) perpendicular to the rotation axis of the radiation device 110. In some embodiments, the one or more imaging radiation sources (or the at least one second imaging radiation source) may be successively arranged and spaced apart by no detector. In some embodiments, the one or more detectors (or the at least one second detector) and the one or more imaging radiation sources (or the at least one second imaging radiation source) may be alternately arranged (e.g., shown in FIG. 8). For example, at least one or two of the one or more imaging radiation sources may be located between two detectors. As another example, at least two detectors may be located between two of the one or more imaging radiation sources.

Figure 7:
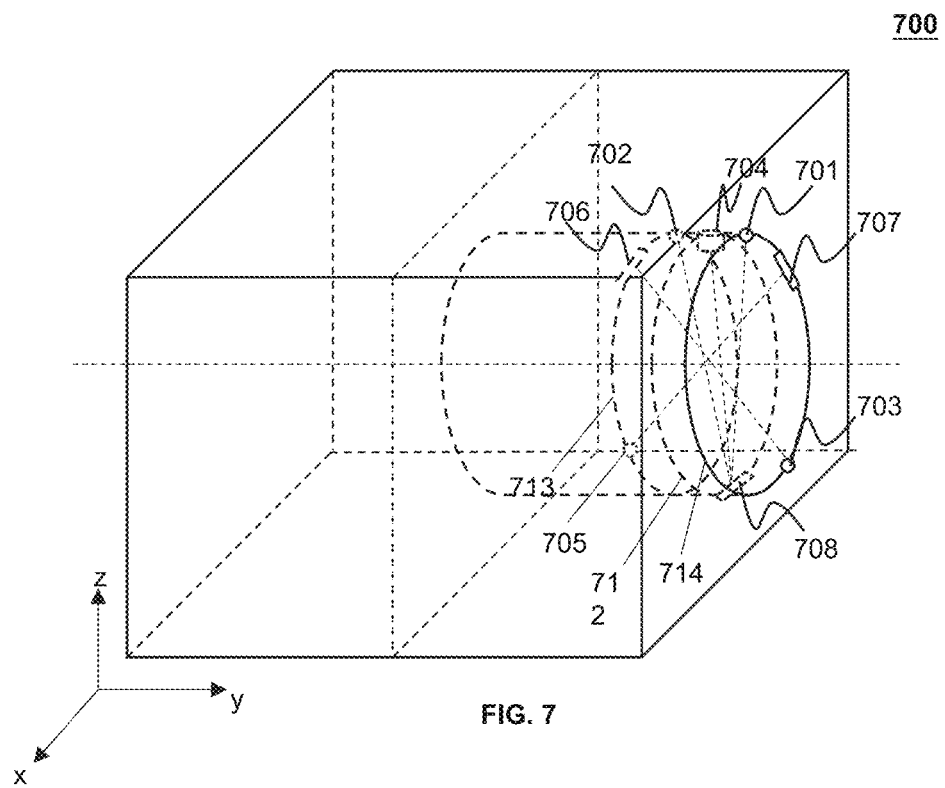

FIG. 7 is a schematic diagram illustrating an exemplary configuration 700 of the radiation device 110 according to some embodiments of the present disclosure. According to configuration 700, four imaging radiation sources 701, 702, 703, and 705, a treatment head 704, and three detectors 706, 707, and 708 may rotate in different rotation planes. For example, the imaging radiation sources 701 and 703, and the detector 707 may be configured to rotate in a rotation plane 714. The treatment head 704 and the detector 708 (e.g., an EPID) may be configured to rotate in a rotation plane (or referred to as a rotation ring or simply a ring) 712. The imaging radiation source 705 and the detector 706 may be configured to rotate in a rotation plane 713. The rotation planes 712, 713, and 714 may be different planes along the rotation axis of the radiation device 110.

As shown in FIG. 7, the detector 706 may be located opposite to the imaging radiation source 703 and configured to detect an imaging beam emitted from the 703. The detector 707 may be located opposite to the imaging radiation source 705 and configured to detect an imaging beam emitted from the 705. The detector 708 may be located opposite to the imaging radiation sources 701 and 702 and the treatment head 704 and configured to detect imaging beam(s) emitted from the 701 and/or 702 and/or a treatment beam emitted from 704.

Figure 8:
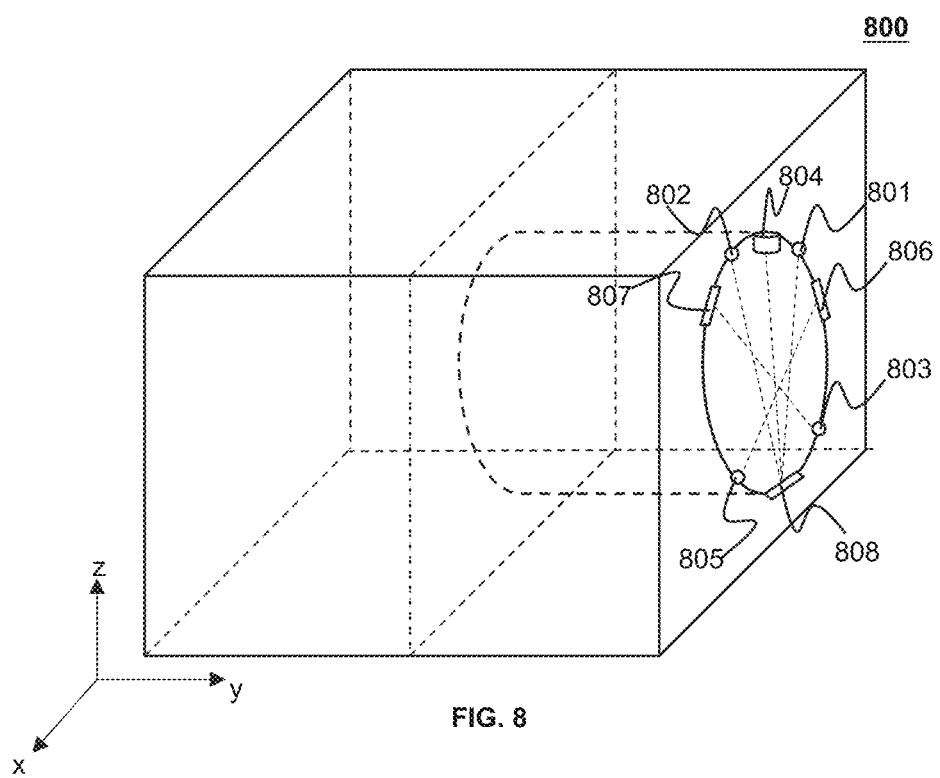

FIG. 8 is a schematic diagram illustrating an exemplary configuration 800 of the radiation device 110 according to some embodiments of the present disclosure. A treatment head 804, imaging radiation sources 801, 803, 805, and 802 and detectors 806, 808, and 807 may be configured to rotate in a same rotation plane. The imaging radiation sources, 801, 803, 805, and 802 and the detectors 806, 808, and 807 may be alternately arranged. In some embodiments, the detector 708 (e.g., an EPID) may be configured to detect at least a portion of imaging beam(s) emitted by the imaging radiation sources 801, 803, 805, and 802 and/or at least a portion of a treatment beam emitted by the treatment head 804.

In some embodiments, at least one of the one or more imaging radiation sources (or the at least one second imaging radiation source) and the treatment head may be configured to rotate in different rotation planes that are parallel to each other and perpendicular to the rotation axis of the radiation device 110. For example, two of the at least one second imaging radiation source may be respectively located on two sides of the treatment head along the rotation axis of the radiation device 110.

In some embodiments, at least one of the one or more imaging radiation sources (or the at least one second imaging radiation source) and the one or more detectors (or the at least one second detector) may be positioned proximal or distal to the maximum treatment field of the treatment head along an emitting direction of a treatment beam emitted by the treatment head.

In some embodiments, similar to the first imaging radiation source and the treatment head, at least two of the one or more imaging radiation sources (or the at least one second imaging radiation source) may be configured to emit the imaging beams concurrently or alternately. In some embodiments, at least one of the one or more imaging radiation sources may be configured to emit the imaging beam while the treatment head is delivering the treatment beam to the object or when a delivery of the treatment beam to the object is paused.

In some embodiments, a first angular projection range of a combination of the one or more static imaging radiation sources (or the at least one second imaging radiation source) may be a portion of a full angular projection range of the radiation system. At least one of the one or more imaging radiation sources (or the at least one second imaging radiation source) may be configured to rotate, while the treatment head is delivering the treatment beam to the object or when a delivery of the treatment beam to the object is paused, to cover a second angular projection range. The first angular projection range and the second angular projection range may constitute the full angular projection range of the radiation device 110.

In some embodiments, one (or referred to as a third imaging radiation source) of the one or more imaging radiation source and a corresponding detector (or referred to as a third detector) of the one or more detectors, collectively referred to as the third image source-third detector group, may be set in a first rotation plane (e.g., rotation plane 712 in FIG. 7, ring 901 in FIG. 9B); the remaining radiation sources and the remaining detectors, collectively referred to as the remaining radiation source-remaining detector group, may be set in a second rotation plane (e.g., rotation plane 713 or 714 in FIG. 7, ring 902 in FIG. 9B); the third image source-third detector group may move in a different rotation plane than the remaining radiation source-remaining detector group without interfering with each other. Therefore, the third imaging radiation source and the third detector may move in the range of 360 degrees along the corresponding rotation ring without collision.

In some embodiments, at least one of one or more remaining radiation sources (including the treatment head and the one or more imaging radiation sources except the third imaging radiation source), or one or more remaining detector (the one or more detectors except the third detector corresponding to the third imaging radiation source) may be configured to move radially away from an isocenter of the radiation system to allow movement of the third imaging radiation source and the third detector in a range of 360 degrees.

In some embodiments, the one or more imaging radiation sources and the one or more detectors may be positioned to move along a same rotation ring. In some embodiments, one (or referred to as a third imaging radiation source) of the one or more imaging radiation sources may be configured to move, along with a corresponding detector (or referred to as a third detector) of the one or more detectors, around a rotation axis of the gantry and independently of the gantry in a first range less than or equal to 360 degrees without collision. In some embodiments, at least one of the remaining radiation sources (including the treatment head and the one or more imaging radiation sources (except the third imaging radiation source) or the one or more detectors (except the third detector corresponding to the third imaging radiation source)) may be configured to move (e.g., move radially away from the isocenter of the radiation system, or move along the y direction) to make room for the independent movement of the third imaging radiation source and the third detector, thereby allowing the independent movement of the third imaging radiation source and the third detector in a second range without collision. The second range may be larger than the first range.

In some embodiments, at least one of the one or more imaging radiation sources may be configured to perform a one-directional rotation (e.g., a clockwise rotation or an anti-clockwise rotation) in a range of 360 degrees. In some embodiments, at least one of the one or more imaging radiation sources may be configured to perform an oscillation in a range of 360 degrees or a limited angle range less than 360 degrees. As used herein, an oscillation refers to moving forward and backward, e.g., along the clockwise direction and then the anti-clockwise direction, or vice versa.

In some embodiments, as described above, the first imaging radiation source may be positioned apart from the treatment head by a certain distance along the rotation axis of the radiation device 110. Thus, the first imaging radiation source may deliver the first imaging beam to image a first region of the object, while the treatment head is delivering the treatment beam towards a second region of the object (e.g., a target region of the object to be treated). In some embodiments, the radiation device 110 may include a collimator (e.g., a secondary collimator). The collimator may include a plurality of leaves forming an aperture configured to collimate the treatment beam to conform to the second region of the object. In some embodiments, the first region (e.g., the heart, the lung, the diaphragm, the bladder, or the rectum of the object) may relate to a motion of the second region (e.g., the chest, the breast, or the abdomen of the object). In some embodiments, the first region may at least partially overlap the second region. In some embodiments, an image of the first region determined based on an imaging dataset corresponding to at least a portion of the first imaging beam detected by a detector of the radiation system 100 may include the second region. The image of the first region may be used not only to monitor the motion of the first region and/or second region but also to monitor a radiotherapy of the second region. In some embodiments, a position of the first imaging radiation source may be adjusted to allow the first region to at least partially overlap the second region. In some embodiments, a radiation range of the first imaging radiation source may be adjusted to allow the first region to at least partially overlap the second region. In some alternative embodiments, the first region may not overlap the second region. For instance, the first region may adjoin the second region, or be spaced apart from the second region.

In some embodiments, when the second region is moved relative to the treatment head due to a motion of an organ of the object, at least one of a position or a shape of the aperture of the collimator may be adjusted such that the collimated treatment beam tracks the second region. In some embodiments, as described above, the first region may relate to the motion of the second region. The processing device 120 may adjust the at least one of a position or the shape of the aperture of the collimator based on the image of the first region. For example, if the second region moves left (e.g., the positive x direction) by a first distance relative to the treatment head due to a motion of an organ of the object, the whole collimator may move left by a second distance corresponding to the first distance. As another example, if the second region moves left (e.g., the positive x direction) by a first distance relative to the treatment head due to a motion of an organ of the object, at least one leaf used to shape the second region of the collimator may move left by a second distance corresponding to the first distance. As a further example, if the second region moves left (e.g., the positive x direction) by a first distance relative to the treatment head due to a motion of an organ of the object, the whole collimator may rotate by a certain degree (e.g., 10 degrees, 30 degrees, 60 degrees, 90 degrees, 180 degrees, 270 degrees) such that the treatment beam tracks the second region after the movement of the second region.

In some embodiments, when the object is moved along a rotation axis of the radiation device 110 relative to the treatment head, e.g., during a radiation treatment of the target region of the object to be treated, at least one of a position and/or a shape of the aperture of the collimator may be adjusted such that the collimated treatment beam tracks the target region of the object to be treated. A position of the aperture of the collimator may move along a same direction as a direction that the object is moved relative to the treatment head. For example, if the object is moved relative to the treatment head by moving the patient support 113 along the rotation axis, a position of the aperture of the collimator may move along a same direction as the patient support 113. As another example, if the object is moved relative to the treatment head by moving the gantry of the radiation system, a position of the aperture of the collimator may move along an opposite direction to a direction along which the gantry of the radiation system moves. In some embodiments, the position and/or the shape of the aperture of the collimator may be adjusted by moving the whole collimator along the rotation axis and/or adjusting one or more leaves of the plurality of leaves of the collimator that are involved in forming the aperture. For example, if the object is moved relative to the treatment head by moving the patient support 113 left (e.g., the positive x direction) by a first distance along the rotation axis, the whole collimator may move left by a second distance corresponding to the first distance. As another example, if the object is moved relative to the treatment head by moving the patient support 113 left (e.g., the positive x direction) by a distance along the rotation axis, the whole collimator may rotate by a certain degree (e.g., 10 degrees, 30 degrees, 60 degrees, 90 degrees, 180 degrees, 270 degrees) such that the treatment beam tracks the second region after the movement.

In some embodiments, after the radiation treatment of the target region to be treated is completed, the object may be moved along the rotation axis of the radiation device 110 to position a next target region to be treated in the radiation system 100. For example, a center of the next target region to be treated may be positioned to (substantially) coincide with the isocenter of the radiation system (e.g., the isocenter of a treatment assembly of the radiation system). Further, at least one of the one or more imaging radiation sources may emit imaging beam(s) towards the next target region to be treated and an image of the next target region to be treated may be generated. In some embodiments, a radiation treatment of the next target region may be guided using the image of the next target region to be treated.

Figure 10A:
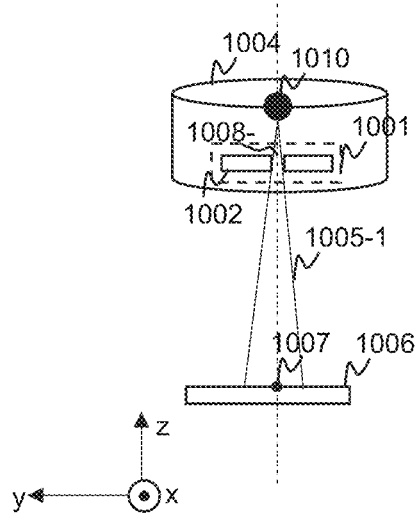
FIGS. 10A-10D are schematic diagrams illustrating exemplary adjustments of an aperture of a collimator according to some embodiments of the present disclosure.
Figure 10B:
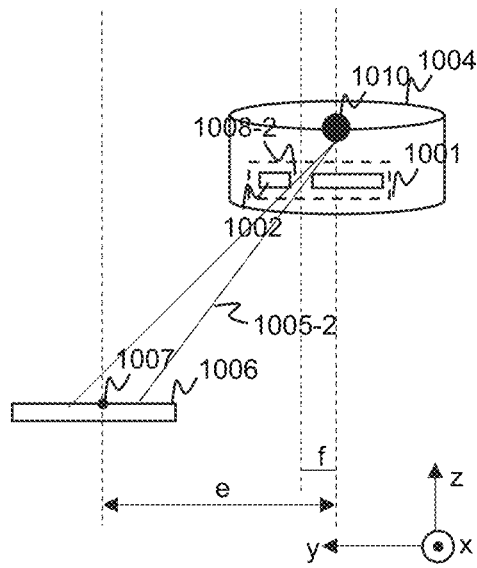

FIGS. 10A-10D are schematic diagrams illustrating exemplary adjustments of an aperture of a collimator according to some embodiments of the present disclosure. As shown in FIG. 10A, leaves 1002 of a collimator 1001 (e.g., a secondary collimator) may form a first aperture 1008-1 and collimate a treatment beam emitted by a treatment radiation source 1010 (e.g., an X-ray target) of a treatment head 1004 to a first collimated treatment beam 1005-1. The first collimated treatment beam 1005-1 may impinge on a region 1007 to be treated of an object 1006 through the first aperture 1008-1. As shown in FIG. 10B, the object 1006 may move along the positive y direction by a first distance (e.g., a distance e). In order to make the treatment beam track the region 1007 to be treated, a position of the whole collimator 1001 and at least one position of at least one of the leaves 1002 may move such that a position of the aperture of the collimator 1001 moves along the positive y direction by a second distance (e.g., a distance f). In such cases, the leaves 1002 of the collimator 1001 may form a second aperture 1008-2 and collimate the treatment beam emitted by a treatment head 1004 to provide a second collimated treatment beam 1005-2. The second collimated treatment beam 1005-2 may impinge on the region 1007 to be treated through the second aperture 1008-2.

Figure 10C:
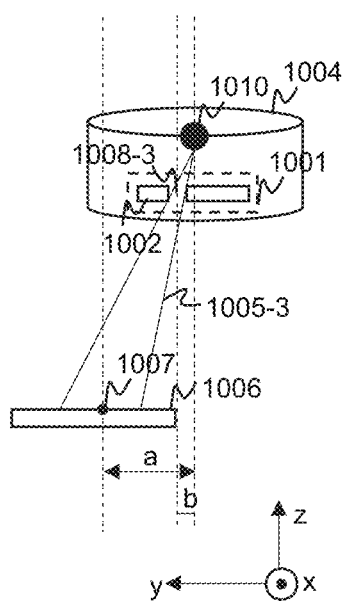

As shown in FIG. 10C, the object 1006 may move along the positive y direction by a first distance (e.g., a distance a). In order to make the treatment beam track the region 1007 to be treated, at least one position of at least one of the leaves 1002 moves such that a position of the aperture of the collimator 1001 moves along the positive y direction by a second distance (e.g., a distance b). In such cases, the leaves 1002 of the collimator 1001 may form a third aperture 1008-3 and collimate the treatment beam emitted by the treatment head 1004 to provide a third collimated treatment beam 1005-3. The third collimated treatment beam 1005-3 may impinge on the region 1007 to be treated through the third aperture 1008-3.

Figure 10D:
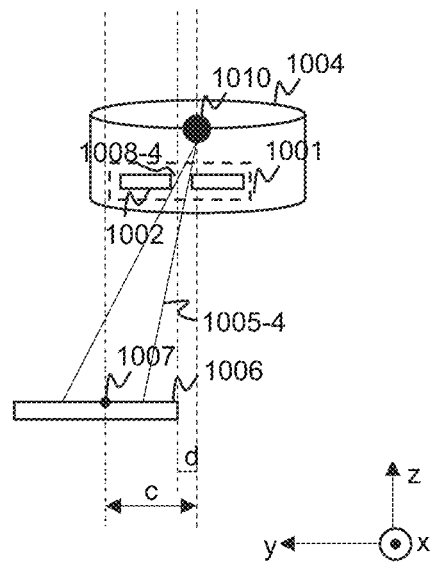

As shown in FIG. 10D, the object 1006 may move along the positive y direction by a first distance (e.g., a distance c). In order to make the treatment beam track the region 1007 to be treated, a position of the whole collimator 1001 moves such that a position of the aperture of the collimator 1001 moves along the positive y direction by a second distance (e.g., a distance d). In such cases, the leaves 1002 of the collimator 1001 may form a fourth aperture 1008-4 and collimate the treatment beam emitted by the treatment head 1004 to provide a fourth collimated treatment beam 1005-4. The fourth collimated treatment beam 1005-4 may impinge on the region 1007 to be treated through the fourth aperture 1008-4.

Figure 10E:
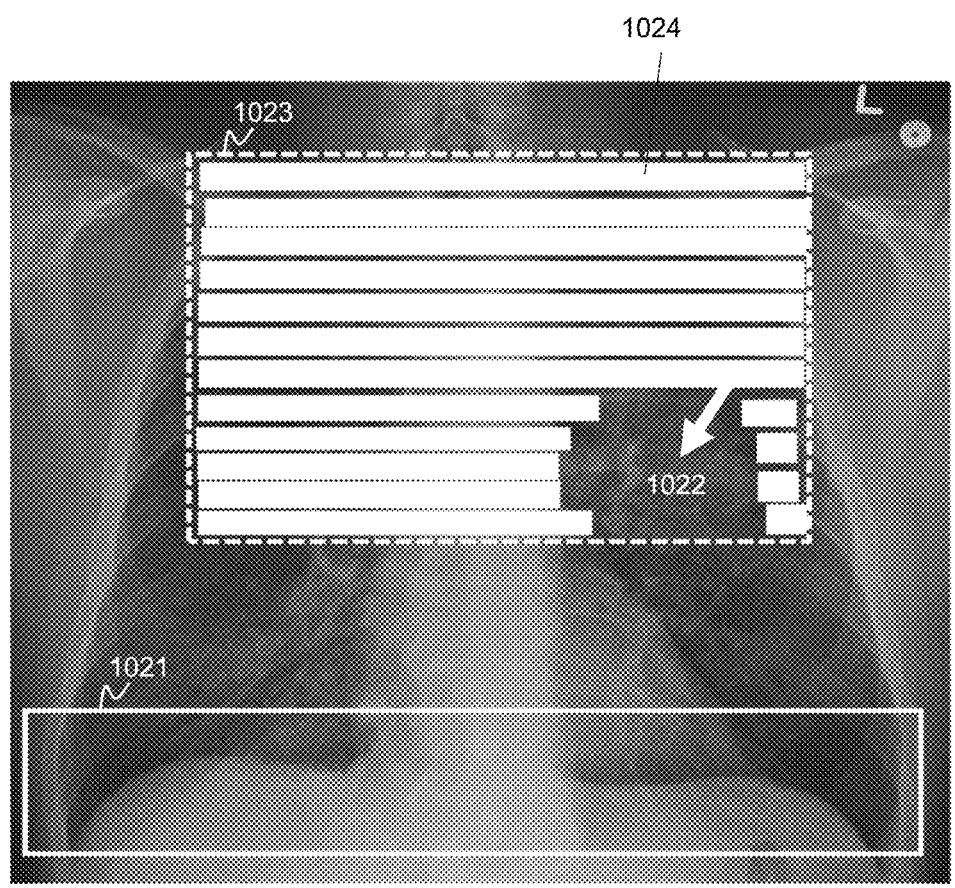
FIGS. 10E-10G are schematic diagrams illustrating exemplary first regions and second regions of an object according to some embodiments of the present disclosure.
Figure 10F:
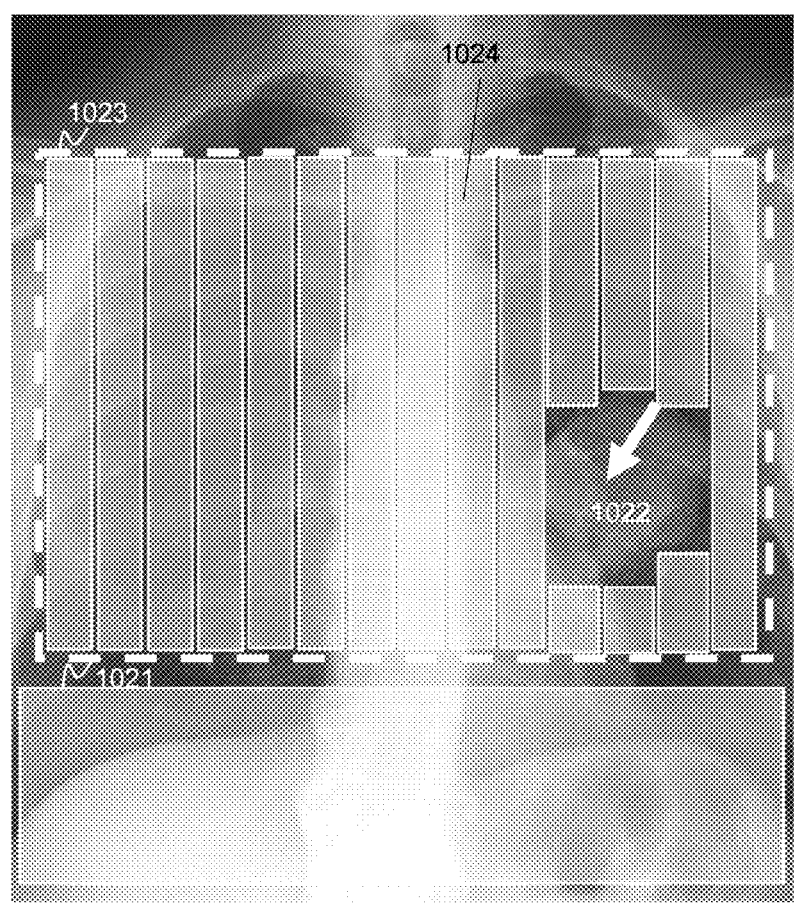
Figure 10G:
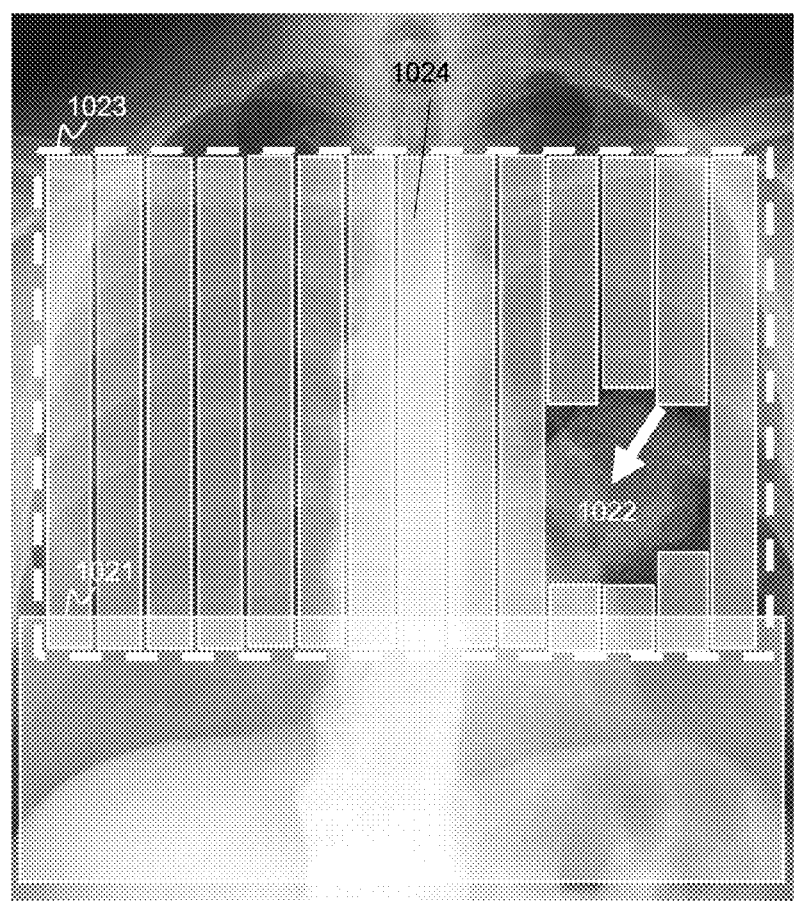

FIGS. 10E-10G are schematic diagrams illustrating exemplary first regions and second regions of an object according to some embodiments of the present disclosure. As shown in FIG. 10E, a first imaging radiation source may deliver a first imaging beam to image a first region 1021 (e.g., the diaphragm) of an object. Leaves 1024 of a collimator 1023 (e.g., a secondary collimator) may be arranged along a y-direction (e.g., the same as the y-direction illustrated in FIGS. 1 and 10A-10D). The leaves may be moveable along an x-direction (e.g., the same as the x-direction illustrated in FIGS. 1 and 10A-10D) perpendicular to the first direction. The collimator 1023 may collimate a treatment beam to conform to a second region 1022 (e.g., the chest) of the object. In some embodiments, a motion of the second region 1022 may be determined based on an image of the first region 1021. A radiation treatment of the second region 1022 may be determined or adjusted based on the image of the first region 1021. As shown in FIGS. 10E and 10F, the first region 1021 does not overlap the second region 1022. Different from FIG. 10E, the leaves 1024 of the collimator 1023 may be movable along the y-direction and arranged along the x-direction in FIG. 10F. Different from FIG. 10E, the leaves 1024 of the collimator 1023 may be movable along the y-direction and arranged along the x-direction, and the first region 1021 overlaps the second region 1022 as illustrated in FIG. 10G.

FIG. 11 is a schematic diagram illustrating exemplary hardware and/or software components of a computing device on which the processing device 120 may be implemented according to some embodiments of the present disclosure. As illustrated in FIG. 11, the computing device 1100 may include a processor 1110, a storage 1120, an input/output (I/O) 1130, and a communication port 1140.

The processor 1110 may execute computer instructions (program code) and perform functions of the processing device 120 in accordance with techniques described herein. The computer instructions may include routines, programs, objects, components, signals, data structures, procedures, modules, and functions, which perform particular functions described herein. For example, the processor 1110 may process data obtained from the radiation device 110, the storage device 130, the terminal 140, or any other component of the radiation system 100. In some embodiments, the processor 1110 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 1100. However, it should be noted that the computing device 1100 in the present disclosure may also include multiple processors, thus operations and/or method steps that are performed by one processor as described in the present disclosure may also be jointly or separately performed by the multiple processors. For example, if in the present disclosure the processor of the computing device 1100 executes both step A and step B, it should be understood that step A and step B may also be performed by two different processors jointly or separately in the computing device 1100 (e.g., a first processor executes step A and a second processor executes step B, or the first and second processors jointly execute steps A and B).

The storage 1120 may store data/information obtained from the radiation device 110, the storage device 130, the terminal 140, or any other component of the radiation system 100. In some embodiments, the storage 1120 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 1120 may store one or more programs and/or instructions to perform exemplary methods described in the present disclosure.

The I/O 1130 may input or output signals, data, or information. In some embodiments, the I/O 1130 may enable a user interaction with the processing device 120. For example, the processing device 120 may display an image through the I/O 1130. In some embodiments, the I/O 1130 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 1140 may be connected to a network (e.g., the network 150) to facilitate data communications. The communication port 1140 may establish connections between the processing device 120 and the radiation device 110, the storage device 130, or the terminal 140. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 1140 may be a standardized communication port, such as RS232, RS485, etc. In some embodiments, the communication port 1140 may be a specially designed communication port. For example, the communication port 1140 may be designed in accordance with the digital imaging and communications in medicine (DICOM) protocol.

Figure 12:
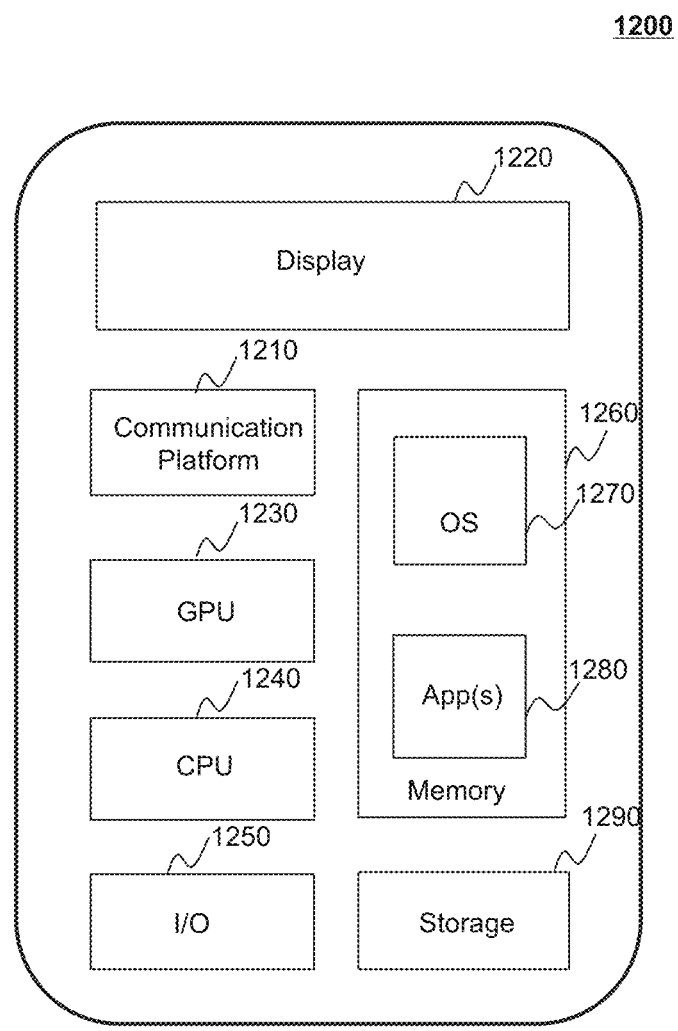
FIG. 12 is a schematic diagram illustrating exemplary hardware and/or software components of a mobile device according to some embodiments of the present disclosure.

FIG. 12 is a schematic diagram illustrating exemplary hardware and/or software components of a mobile device on which the terminal 140 may be implemented according to some embodiments of the present disclosure. As illustrated in FIG. 12, the mobile device 1200 may include a communication platform 1210, a display 1220, a graphics processing unit (GPU) 1230, a central processing unit (CPU) 1240, an I/O 1250, a memory 1260, and a storage 1290. In some embodiments, any other suitable component, including a system bus or a controller (not shown), may also be included in the mobile device 1200. In some embodiments, a mobile operating system 1270 (e.g., iOS, Android, Windows Phone, etc.) and one or more applications 1280 may be loaded into the memory 1260 from the storage 1290 in order to be executed by the CPU 1240. The applications 1280 may include a browser or any other suitable mobile apps for receiving and rendering information relating to radiation therapy or other information from the processing device 120. User interactions with the information stream may be achieved via the I/O 1250 and provided to the processing device 120 and/or other components of the radiation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the radiation therapy as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 13:
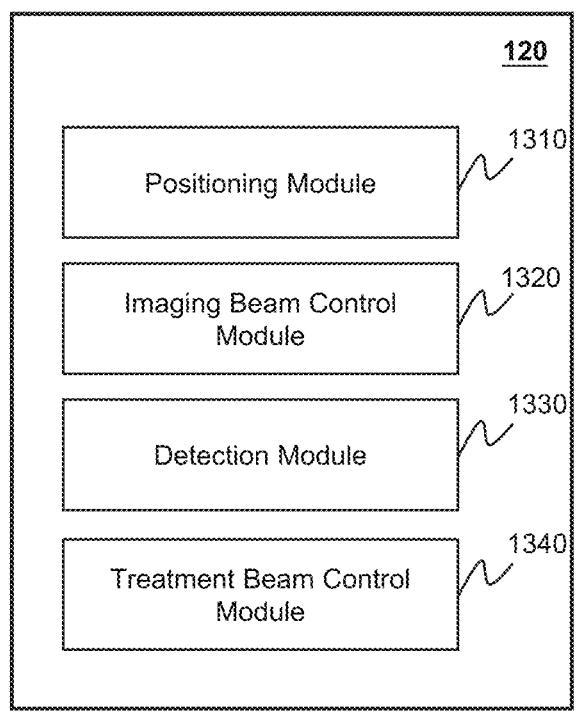
FIG. 13 is a block diagram illustrating an exemplary processing device according to some embodiments of the present disclosure.

FIG. 13 is a block diagram illustrating an exemplary processing device according to some embodiments of the present disclosure. The processing device 120 may include a positioning module 1310, an imaging beam control module 1320, a detection module 1330, and a treatment beam control module 1340.

The positiong module 1310 may be configured to cause an object (e.g., a patient) to be positioned in a radiation system (e.g., the radiation system 100). In some embodiments, a center of a region to be treated (or a target volume) of the object may be aligned with an isocenter of the radiation system.

The imaging beam control module 1320 may be configured to cause at least one imaging radiation source (e.g., the first imaging radiation source, the at least one second imaging radiation source illustrated in FIGS. 1-10G) of the radiation system to deliver at least one imaging beam to the object.

The detection module 1330 may be configured to obtain at least one imaging dataset (e.g., projection data) corresponding to at least a portion of each of the at least one imaging beam detected by at least one of one or more detectors (e.g., the first detector, the at least one second detector illustrated in FIGS. 1-10G) of the radiation system. In some embodiments, the detection module 1330 may generate an image (e.g., a 3D image) (or referred to as a reference image) associated with the object based on at least a portion of the at least one first imaging dataset. In some embodiments, the detection module 1330 may reconstruct the reference image using a reconstruction algorithm. For example, the at least one imaging beam may include a CT imaging beam of a relatively large fan angle emitted by a CT imaging radiation source of the radiation system. The detection module 1330 may reconstruct the reference image based on an imaging dataset corresponding to the CT imaging beam of the relatively large fan angle. An imaging dataset corresponding to a CT imaging beam of a relatively large fan angle can be used to reconstruct a 3D image. As another example, the at least one imaging beam may include two or more imaging beams that are emitted by two or more imaging radiation sources of the radiation system and from two or more views of the object. The detection module 1330 may reconstruct the reference image based on two or more imaging datasets (e.g., projection data) corresponding to the two or more imaging beams from the two or more views of the object.

The treatment beam control module 1340 may be configured to cause a treatment head (e.g., the treatment head illustrated in FIGS. 1-10G) of the radiation system to deliver a treatment beam to the object. The treatment beam may be delivered to the target volume of the object. In some embodiments, the position of the target volume may change with time due to various motions of organs of the object, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. In some embodiments, the whole object may be moved along a direction (e.g., a rotation axis of a radiation device of the treatment system).

In some embodiments, the treatment beam control module 1340 may cause an imaging of the object to be performed during the radiotherapy. For example, at least a portion of the treatment beam may be detected by a detector (e.g., an EPID) to generate a second imaging dataset (e.g., projection data) at a first time point during the radiotherapy. The treatment beam control module 1340 may generate a second image based on at least a portion of the second imaging dataset. The treatment beam control module 1340 may generate at least one third imaging dataset by causing another at least one imaging beam to be delivered to the object by at least one imaging radiation source at a second time point same as or different from the first time point during the radiotherapy. The treatment beam control module 1340 may generate at least one third image based on at least a portion of the at least one third imaging dataset. For example, the treatment beam control module 1340 may generate a third image (e.g., a 2D image, a 3D image) based on at least a portion of each of the at least one third imaging dataset. As another example, the treatment beam control module 1340 may generate a third image based on two or more of the at least one third imaging dataset that are from two or more views of the object. In some embodiments, the treatment beam control module 1340 may generate a fourth image based on at least a portion of the second imaging dataset and at least a portion of the at least one third imaging dataset. The reference image, the second image, the at least one third image, and/or the fourth image may be used to monitor at least one of the position and/or the motion (or movement) of the target volume during the radiotherapy, a change thereof, or a rate of change thereof.

In some embodiments, the treatment beam control module 1340 may determine, based on at least one of the reference image, the second image, the at least one third image, or the fourth image, whether any change or adjustment is needed with respect to the radiotherapy. In some embodiments, when detecting a movement or change of the target volume, the treatment beam control module 1340 may adjust a delivery of the treatment beam or a position of the object based on the at least one of the reference image, the second image, the at least one third image, or the fourth image. For example, the treatment beam control module 1340 may adjust the delivery of the treatment beam or the position of the object by adjusting at least one machine parameter of a radiation device of the radiation system. In some embodiments, the treatment beam control module 1340 may adjust the position of the target volume with respect to the treatment beam to allow the treatment beam towards the target volume. In some embodiments, the treatment beam control module 1340 may adjust a direction of the treatment beam to allow the treatment beam toward the target volume. In some embodiments, the treatment beam control module 1340 may adjust the treatment plan (e.g., a radiation dose of the target volume, a radiation time of the target volume) and deliver an adjusted treatment beam to the object from the treatment head and based on the adjusted treatment plan. In some embodiments, the treatment beam control module 1340 may cause the treatment head to pause the delivery of the treatment beam. For example, the treatment beam control module 1340 may pause the delivery of the treatment beam, and then adjust the treatment head to target at the position of the moved or changed target volume. As another example, the treatment beam control module 1340 may pause the delivery of the treatment beam, and then adjust the position of the target volume with respect to the treatment beam to make the treatment beam target at the target volume. After the delivery of the treatment beam or the position of the object is adjusted, the treatment head may resume the delivery of the treatment beam. In some embodiments, when detecting the movement or change of the target volume, the treatment head may terminate the delivery. In some embodiments, the treatment beam control module 1340 may generate a notification based on the detected movement or change of the target volume. In some embodiments, the notification may include information of the movement or change of the target volume. The notification may be in a form of text, video, audio, etc.

In some embodiments, the treatment beam control module 1340 may determine whether an unpredicted motion of the object exists based on at least one of the reference image, the second image, the at least one third image, or the fourth image. In response to determining that an unpredicted motion of the object exists, the treatment beam control module 1340 may cause the treatment head to pause the delivery of the treatment beam. For instance, the treatment beam control module 1340 may determine whether the object has ceased a planned breathhold. In response to determining that the object has ceased the planned breathhold, the treatment beam control module 1340 may cause the treatment head to pause the delivery of the treatment beam.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module (not shown in FIG. 13). The storage module may be configured to store data generated during any process performed by any component of in the processing device 120. As another example, each of the components of the processing device 120 may include a storage apparatus. Additionally or alternatively, the components of the processing device 120 may share a common storage apparatus.

Figure 14:
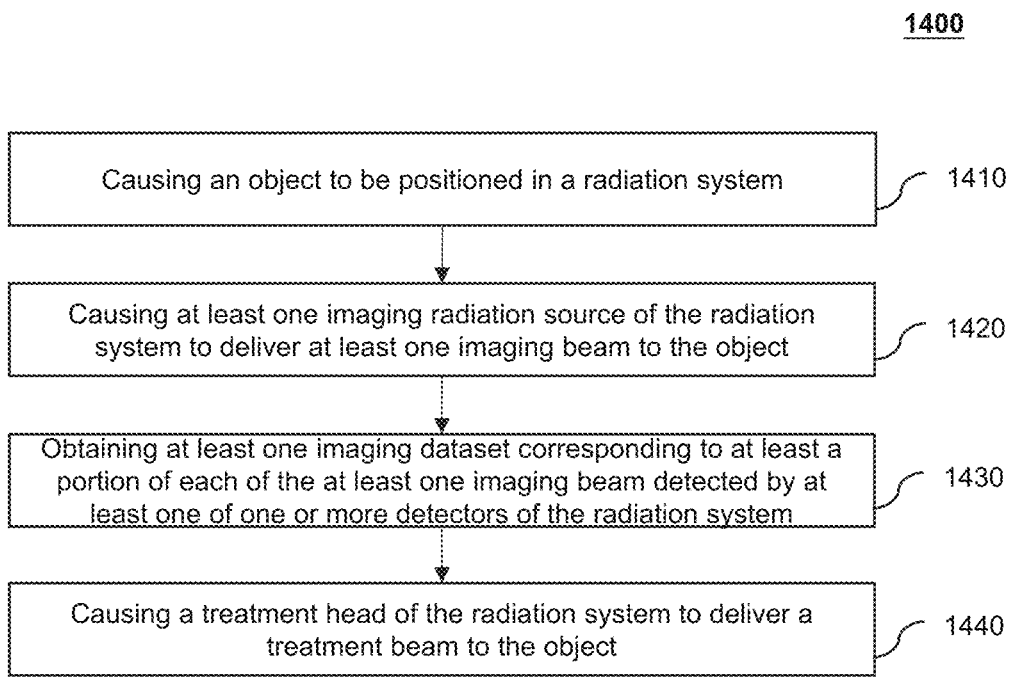
FIG. 14 is a flowchart illustrating an exemplary imaging process according to some embodiments of the present disclosure.

FIG. 14 is a flowchart illustrating an exemplary imaging process according to some embodiments of the present disclosure. The process 1400 may be implemented in the radiation system 100 illustrated in FIG. 1. For example, the process 1400 may be stored in the storage device 130 and/or the storage 1120 in the form of instructions (e.g., an application), and invoked and/or executed by the processing device 120 (e.g., the processor 1110 illustrated in FIG. 11, or one or more modules in the processing device 120 illustrated in FIG. 13). The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1410, the processing device 120 (e.g., the positioning module 1310) may cause an object (e.g., a patient) to be positioned in a radiation system (e.g., the radiation system 100). In some embodiments, a center of a region to be treated of the object may be aligned with an isocenter of the radiation system by the positioning operation. For example, the isocenter of the radiation system may include an isocenter of a treatment assembly of the radiation system or an isocenter of an imaging assembly of the radiation system.

In 1420, the processing device 120 (e.g., the imaging beam control module 1320) may cause at least one imaging radiation source (e.g., the first imaging radiation source, the at least one second imaging radiation source illustrated in FIGS. 1-10G) of the radiation system to deliver at least one imaging beam to the object. Details regarding the at least one imaging beam and the at least one imaging radiation source can be found elsewhere in the present disclosure (e.g., descriptions in connection with FIGS. 1-10G).

In 1430, the processing device 120 (e.g., the detection module 1330) may obtain at least one imaging dataset (e.g., projection data) corresponding to at least a portion of each of the at least one imaging beam detected by at least one of one or more detectors (e.g., the first detector, the at least one second detector illustrated in FIGS. 1-10G) of the radiation system. In some embodiments, the processing device 120 may generate an image (e.g., a 3D image) (or referred to as a reference image) associated with the object based on at least a portion of the at least one first imaging dataset. In some embodiments, the processing device 120 may reconstruct the reference image using a reconstruction algorithm. For example, the reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. For example, the at least one imaging beam may include a CT imaging beam of a relatively large fan angle emitted by a CT imaging radiation source of the radiation system. The processing device 120 may reconstruct the reference image based on an imaging dataset corresponding to the CT imaging beam of the relatively large fan angle. An imaging dataset corresponding to a CT imaging beam of a relatively large fan angle can be used to reconstruct a 3D image. As another example, the at least one imaging beam may include two or more imaging beams that are emitted by two or more imaging radiation sources of the radiation system and from two or more views of the object. The processing device 120 may reconstruct the reference image based on two or more imaging datasets corresponding to the two or more imaging beams from the two or more views of the object.

In some embodiments, the reference image may be used to determine a treatment plan of a radiotherapy on a target volume (e.g., a region to be treated) of the object. In some embodiments, the reference image may be used to adjust a planned treatment plan of the target volume determined based on a planned image of the object. For illustration purposes, the processing device 120 may generate a registration result by registering the reference image and the plan image and adjust the treatment plan based on the registration result. Merely by way of example, a difference between one parameter (e.g., a position of a tumor, a contour of a tumor) of the planned treatment plan and a corresponding parameter determined based on the registration result exceeds a threshold, the processing device 120 may adjust the parameter accordingly. As another example, the processing device 120 may supplement at least one new parameter (a position of a newly grown tumor, a contour of a newly grown tumor) determined based on the registration result.

In 1440, the processing device 120 (e.g., the treatment beam control module 1340) may cause a treatment head (e.g., the treatment head illustrated in FIGS. 1-10G) of the radiation system to deliver a treatment beam to the object. The treatment beam may be delivered to the target volume of the object. In some embodiments, the position of the target volume may change with time due to various motions of organs of the object, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. In some embodiments, the whole object may be moved along a direction (e.g., a rotation axis of a radiation device of the treatment system).

In some embodiments, the processing device 120 may cause an imaging of the object to be performed during the radiotherapy. For example, at least a portion of the treatment beam may be detected by a detector (e.g., an EPID) to generate a second imaging dataset (e.g., projection data) at a first time point during the radiotherapy. The processing device 120 may generate a second image based on at least a portion of the second imaging dataset. The processing device 120 may generate at least one third imaging dataset by causing another at least one imaging beam to be delivered to the object by at least one imaging radiation source at a second time point same as or different from the first time point during the radiotherapy. The processing device 120 may generate at least one third image based on at least a portion of the at least one third imaging dataset. For example, the processing device 120 may generate a third image (e.g., a 2D image, a 3D image) based on at least a portion of each of the at least one third imaging dataset. As another example, the processing device 120 may generate a third image based on two or more of the at least one third imaging dataset that are from two or more views of the object. In some embodiments, the processing device 120 may generate a fourth image based on at least a portion of the second image dataset and at least a portion of the at least one third imaging dataset. The reference image, the second image, the at least one third image, and/or the fourth image may be used to monitor at least one of the position and/or the motion (or movement) of the target volume during the radiotherapy, a change thereof, or a rate of change thereof.

In some embodiments, the processing device 120 may determine, based on at least one of the reference image, the second image, the at least one third image, or the fourth image, whether any change or adjustment is needed with respect to the radiotherapy. In some embodiments, when detecting a movement or change of the target volume, the processing device 120 may adjust a delivery of the treatment beam or a position of the object based on the at least one of the reference image, the second image, the at least one third image, or the fourth image. For example, the processing device 120 may adjust the delivery of the treatment beam or the position of the object by adjusting at least one machine parameter of a radiation device of the radiation system. In some embodiments, the processing device 120 may adjust the position of the target volume with respect to the treatment beam to allow the treatment beam towards the target volume. In some embodiments, the processing device 120 may adjust a direction of the treatment beam to allow the treatment beam toward the target volume. In some embodiments, the processing device 120 may adjust the treatment plan (e.g., a radiation dose of the target volume, a radiation time of the target volume) and deliver an adjusted treatment beam to the object from the treatment head and based on the adjusted treatment plan. In some embodiments, the processing device 120 may cause the treatment head to pause the delivery of the treatment beam. For example, the processing device 120 may pause the delivery of the treatment beam, and then adjust the treatment head to target at the position of the moved or changed target volume. As another example, the processing device 120 may pause the delivery of the treatment beam, and then adjust the position of the target volume with respect to the treatment beam to make the treatment beam target at the target volume. After the delivery of the treatment beam or the position of the object is adjusted, the treatment head may resume the delivery of the treatment beam. In some embodiments, when detecting the movement or change of the target volume, the treatment head may terminate the delivery. In some embodiments, the processing device 120 may generate a notification based on the detected movement or change of the target volume. In some embodiments, the notification may include information of the movement or change of the target volume. The notification may be in a form of text, video, audio, etc.

In some embodiments, the processing device 120 may determine whether an unpredicted motion of the object exists based on at least one of the reference image, the second image, the at least one third image, or the fourth image. In response to determining that an unpredicted motion of the object exists, the processing device 120 may cause the treatment head to pause the delivery of the treatment beam. For instance, the processing device 120 may determine whether the object has ceased a planned breathhold. In response to determining that the object has ceased the planned breathhold, the processing device 120 may cause the treatment head to pause the delivery of the treatment beam.

According to the systems and methods described in the present disclosure, during a radiotherapy on a target volume, the processing device 120 may automatically generate and/or analyze images (e.g., the reference image, the second image, the at least one third image, or the fourth image) to record the radiotherapy, monitor the position of the target volume, assess the change of the position of the target volume, and/or determine how to proceed further with the radiotherapy (e.g., to continue the radiotherapy as planned, to continue the radiotherapy with a revised plan, or to terminate the radiotherapy, etc.). In some embodiments, the monitoring, assessment, and/or adjustment may be performed semi-automatically with the input of a user (e.g., a doctor). For instance, the processing device 120 may transmit the images to be presented on the terminal 140 (e.g., a display) so that the user may analyze the images and provide an instruction as to how to proceed further with the radiotherapy (e.g., to continue the radiotherapy as planned, to continue the radiotherapy with a revised plan, or to terminate the radiotherapy, etc.). As another example, the processing device 120 may first analyze the images and determine if any change occurs in the target volume and how much the change is. The processing device 120 may determine accordingly if any adjustment in the radiotherapy is needed. If the change of the target volume or the adjustment needed in the radiotherapy is within a threshold, the processing device 120 may adjust automatically. In some embodiments, a notification may be generated when the processing device 120 makes such a determination. If the change of the target volume or the adjustment needed in the radiotherapy is not within a threshold, the processing device 120 may generate a notification to, e.g., the user to seek instructions from the user as to how to proceed further.

In some application scenarios, before a radiotherapy of a target volume of an object, the processing device 120 may generate a first pre-treatment image (e.g., a 3D image) by causing an imaging radiation source (e.g., a CT imaging radiation source) of one or more imaging radiation source of a radiation system (e.g., the radiation system 100) to emit a first pre-treatment imaging beam to the object. The processing device 120 may determine position information (e.g., a position thereof, a contour thereof) of the target volume of the object based on the first pre-treatment image. Further, the processing device 120 may cause the target volume of the object to be positioned in the radiation system according to the position information. In some embodiments, a center of the target volume may be aligned with an isocenter of the radiation system. For example, the isocenter of the radiation system may include an isocenter of a treatment assembly of the radiation system or an isocenter of an imaging assembly of the radiation system.

In some embodiments, the processing device 120 may generate a second pre-treatment image by causing at least one of the one or more imaging radiation sources to emit at least one second pre-treatment imaging beam toward the object. For example, the second pre-treatment image may be a multi-energy image. In some embodiments, the at least one second pre-treatment imaging beam may include at least two second pre-treatment imaging beams that are of different energy levels. In some embodiments, the at least two second pre-treatment imaging beams of different energy levels may be emitted by at least two of the one or more imaging radiation sources of the radiation system. In some embodiments, the at least two second pre-treatment imaging beams of different energy levels may be emitted by one of the plurality of imaging sources that is configured to emit imaging beams of different energy levels. For example, the imaging source may emit the imaging beams of different energy levels by adjusting a voltage of the imaging source.

In some embodiments, a detector (e.g., a layer detector) may detect signals resulting from the second pre-treatment imaging beams impinging on the detector. The detector may determine the imaging sources by which the impinging imaging beams are emitted. The imaging source determination may be made based on the energy levels or intensities of the signals that correspond to the energy levels of the second pre-treatment imaging beams, the entry angles of the second pre-treatment imaging beams at which the second pre-treatment imaging beams impinge on the detector, and/or the detection regions on the detection where the second pre-treatment imaging beams impinge.

In some embodiments, if the at least one imaging radiation source includes the CT imaging radiation source, the CT imaging source may be adjustably collimated by a collimator of the radiation system. A first fan angle of the first pre-treatment imaging beam may be larger than a second fan angle of one of the at least one second pre-treatment imaging beam emitted by the CT imaging radiation source. The second pre-treatment imaging beam emitted by the CT imaging source may be of the second fan angle achieved by adjusting the aperture of the collimator of the CT imaging source.

The processing device 120 may generate the second pre-treatment image based on an imaging dataset corresponding to each of the at least two second pre-treatment imaging beams of different energy levels detected by the detector. For instance, the processing device 120 may generate at least two images (e.g., a 2D image) based on at least two imaging datasets corresponding to the at least two imaging beams and generate the second pre-treatment image by fusing the at least two images, e.g., according to a fusion algorithm. For example, the fusion algorithm may include an averaging algorithm, a Brovey algorithm, a principal component analysis (PCA) algorithm, or the like, or any combination thereof.

Further, the processing device 120 may adjust a treatment plan of the target volume of the object based on the first pre-treatment image and the second pre-treatment image. In some embodiments, the processing device 120 may generate a fused image by fusing the first pre-treatment image and the second pre-treatment image. During the image fusion, detailed contour information of the target region and/or tissues (e.g., soft tissues) surrounding the target volume may be extracted. Thus, the fused image may have an improved contrast of the tissues surrounding the target volume. The processing device 120 may determine information of the target volume in the fused image. For example, the information of the target volume may include a contour of the target volume in the fused image, a contour of a tissue surrounding the target volume in the fused image, etc. The processing device 120 may adjust the treatment plan of the target volume of the object based on the information of the target volume. In some embodiments, the processing device 120 may identify a change (e.g., a contour thereof) of the target volume based on the information of the target volume in the fused image, compared to the planned information (e.g., a planned contour) of the target volume determined based on, e.g., a plan image of the object. In some embodiments, the plan image may be used to determine the treatment plan of the object. In response to determining that the change exceeds a first threshold, the processing device 120 may adjust the treatment plan based on the information of the target volume in the fused image or the change. In some embodiments, in response to determining that the change exceeds a second threshold larger than the first threshold, the processing device 120 may determine a new treatment plan based on the fused image.

In some application scenarios, the processing device 120 may cause a treatment head of a radiation system (e.g., the radiation system 100) to deliver a treatment beam to a target volume of an object in a treatment session based on a treatment plan of the object. The treatment beam may be delivered to the target volumen. During a treatment session, the processing device 120 may generate a first group of images (e.g., 2D images) of the object by causing, at a first time point, at least two of one or more imaging radiation sources of the radiation system to deliver at least two imaging beams to the object to provide views (e.g., a front view, a side view, a lateral view) of the object from different directions/view angles. In some embodiments, the processing device 120 may generate a second group of images (e.g., 2D images) of the object by causing, at a second time point different from the first time point, the at least two imaging radiation sources of the radiation system to deliver another at least two imaging beams to the object. The first group of images and the second group of images may be used to track a change of a position of the target volume. In response to determining that the change exceeds a threshold, the processing device 120 may adjust the delivery of the treatment beam or the position of the target volume according to the process for adjusting the delivery of the treatment beam or the position of the target volume described elsewhere in the present disclosure. See, e.g., operation 1440 in FIG. 14 and the description thereof, which are not repeated here.

In some application scenarios, before a radiotherapy of a target volume of an object, the processing device 120 may generate a pre-treatment image (e.g., a 3D image) by causing an imaging radiation source (e.g., a CT imaging radiation source of a radiation system (e.g., the radiation system 100) to emit a pre-treatment imaging beam to the object. During the radiotherapy, the processing device 120 may cause a treatment head of the radiation system to deliver at least one treatment beam to the target volume of the object according to a treatment plan of the object. The processing device 120 may generate at least one treatment image based on at least a portion of the at least one treatment beam detected by a detector (e.g., an EPID) of the radiation system. The processing device 120 may determine whether a delivery of the treatment beam conforms to a planned delivery of a planned treatment beam of the treatment plan based on the pre-treatment image and the at least one treatment image.

In some embodiments, the at least one treatment image may include one treatment image (e.g., a 2D image). The processing device 120 may determine a reference treatment image (e.g., a 2D image) based on the pre-treatment image and the treatment plan of the object. For example, the treatment image and the reference treatment image may be both two-dimensional and from a same view of the object. In some embodiments, the processing device 120 may determine a reference radiation dose distribution (e.g., a 2D radiation dose distribution) of the treatment beam in the object and an actual radiation dose distribution (e.g., a 2D radiation dose distribution) of the treatment beam in the object. The reference radiation dose distribution may be determined based on the reference treatment image. The actual radiation dose distribution may be determined based on the treatment image. Further, the processing device 120 may generate a comparison result by comparing the reference radiation dose distribution and the actual radiation dose distribution. The processing device 120 may determine whether the delivery of the treatment beam conforms to the planned treatment beam of the treatment plan based on the comparison result. In response to determining that the comparison result includes that a difference between the reference radiation dose distribution and the actual radiation dose distribution exceeds a threshold, the processing device 120 may determine that the delivery of the treatment beam fails to conform to the planned treatment beam of the treatment plan. In some embodiments, the processing device 120 may further adjust the delivery of the treatment beam or a position of the target volume based on the comparison result according to the process for adjusting the delivery of the treatment beam or the position of the target volume described elsewhere in the present disclosure. See, e.g., operation 1440 in FIG. 14 and the description thereof, which are not repeated here.

In some embodiments, the at least one treatment image may include a plurality of treatment images from at least two different views of the object. The processing device 120 may determine a radiation dose distribution (e.g., a 3D radiation dose distribution) (also referred to as an actual radiation dose distribution) of the treatment beam in the object based on the pre-treatment image and the plurality of treatment images. The processing device 120 may retrieve a planned radiation dose distribution from the treatment plan. The processing device 120 may generate a comparison result by comparing the actual radiation dose distribution of the treatment beam and a planned radiation dose distribution (e.g., a 3D radiation dose distribution) in the object. Further, the processing device 120 may determine whether the delivery of the treatment beam conforms to the planned treatment beam of the treatment plan based on the comparison result. In some embodiments, in response to determining that a difference between the actual radiation dose distribution and the planned radiation dose distribution exceeds a threshold, the processing device 120 may determine that the delivery of the treatment beam fails to conform to the planned treatment beam of the treatment plan. In some embodiments, the processing device 120 may further adjust the delivery of the treatment beam or the position of the target volume according to the process for adjusting the delivery of the treatment beam or the position of the target volume described elsewhere in the present disclosure. See, e.g., operation 1440 in FIG. 14 and the description thereof, which are not repeated here.

According to some embodiments of the present disclosure, the radiation system described (e.g., the radiation system 100) in FIGS. 1-14 may include a treatment assembly, an imaging assembly, and a gantry. The treatment assembly may include a treatment head configured to deliver a treatment beam to an object and a first assistance assembly configured to facilitate a delivery of the treatment beam. The imaging assembly may include a first imaging radiation source configured to direct a first imaging beam toward the object, a first detector configured to detect at least a portion of the first imaging beam, and a second assistance assembly configured to facilitate a delivery of the first imaging beam. More descriptions regarding the treatment assembly and the imaging assembly may be found elsewhere in the present disclosure. See, for example, FIGS. 1-14, and the descriptions thereof.

In some embodiments, the gantry may have a rotation axis (e.g., the rotation axis 208 illustrated in FIG. 2 or FIG. 3). The treatment assembly and the imaging assembly may be supported on the gantry. The treatment head, the first imaging radiation source, and the first detector may be disposed on a same side of the first assistance assembly and the second assistance assembly along the rotation axis. For instance, the treatment head, the first imaging radiation source, and the first detector may be disposed on a first side of the gantry, while the first assistance assembly and the second assistance assembly may be disposed on a second side of the gantry, in which the first side and the second side are spaced along the rotation axis of the gantry. See, e.g., FIGS. 2 and 3. In some embodiments, the treatment head, the first imaging radiation source, and the first detector may be disposed in a first gantry portion of the gantry. The first assistance assembly and the second assistance assembly may be disposed in a second gantry portion of the gantry that is located next to the first gantry portion along the rotation axis. For example, the first gantry portion may be disposed on a right side (e.g., the positive y direction) of the second gantry portion, that is, the treatment head, the first imaging radiation source, and the first detector may be disposed on a right side (e.g., the positive y direction) of the first assistance assembly and the second assistance assembly in FIG. 2 or FIG. 3. More descriptions regarding the gantry may be found elsewhere in the present disclosure. See, for example, FIGS. 1-14, and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system comprising:
   a treatment assembly including a treatment head configured to deliver a treatment beam to an object and a first assistance assembly configured to facilitate a delivery of the treatment beam;
   an imaging assembly including a first imaging radiation source configured to direct a first imaging beam toward the object, a first detector configured to detect at least a portion of the first imaging beam, and a second assistance assembly configured to facilitate a delivery of the first imaging beam;
   a gantry including a first gantry portion and a second gantry portion, the treatment head, the first imaging radiation source, and the first detector being disposed on the first gantry portion that has a rotation axis; and the second gantry portion being located next to the first gantry portion along the rotation axis, the first assistance assembly and the second assistance assembly being housed within the second gantry portion.

2. The system of claim 1, wherein the treatment head, the first imaging radiation source, and the first detector are configured to rotate in a same rotation plane that is perpendicular to the rotation axis.

3. The system of claim 1, wherein
the treatment head is configured to rotate in a first rotation plane perpendicular to the rotation axis,
the first imaging radiation source and the first detector are configured to rotate in a second rotation plane that is perpendicular to the rotation axis, and
the first rotation plane is different from the second rotation plane.

4. The system of claim 3, wherein the first imaging radiation source and the first detector are located between the second gantry portion and the treatment head.

5. The system of claim 1, wherein the first imaging radiation source is located as close as possible to the treatment head without interference with the treatment beam.

6. The system of claim 1, wherein the delivery of the treatment beam and the delivery of the first imaging beam alternate.

7. The system of claim 6, wherein
the first gantry portion rotates at a first speed when the first imaging beam is delivered,
the first gantry portion rotates at a second speed when the treatment beam is delivered, and
the first speed is faster than the second speed.

8. The system of claim 1, wherein the delivery of the treatment beam and the delivery of the first imaging beam are concurrent, the first imaging radiation source, the first detector, and the treatment head rotate at a third speed when the first imaging beam and the treatment beam are delivered.

9. The system of claim 1, wherein there is an angular offset between the first imaging radiation source and the treatment head.

10. The system of claim 1, wherein the imaging assembly includes
at least one second imaging radiation source each of which is configured to emit a second imaging beam towards the object,
at least one second detector configured to detect at least a portion of the at least one second imaging beam, and
the at least one second imaging radiation source and the at least one second detector are mounted on the first gantry portion.

11. The system of claim 10, wherein at least one of the at least one second imaging radiation source and the treatment head are configured to rotate in a same rotation plane perpendicular to the rotation axis.

12. The system of claim 10, wherein at least one of the at least one second imaging radiation source and the treatment head are configured to rotate in different rotation planes each of which is perpendicular to the rotation axis.

13. A method comprising:
causing an object to be positioned in a radiation system, the radiation system including:
a treatment assembly including a treatment head and a first assistance assembly configured to facilitate a delivery of a treatment beam from the treatment head;
an imaging assembly including an imaging radiation source, a detector, and a second assistance assembly configured to facilitate a delivery of an imaging beam from the imaging radiation source; and
a gantry including a first gantry portion and a second gantry portion,
the first gantry portion having a rotation axis, the treatment head, the imaging radiation source, and the detector being mounted on the first gantry portion; and
the second gantry portion being located next to the first gantry portion along the rotation axis, the first assistance assembly and the second assistance assembly being housed within the second gantry portion;
causing the imaging radiation source to deliver an imaging beam to the object;
obtaining an imaging dataset corresponding to at least a portion of the imaging beam detected by the detector; and
causing the treatment head to deliver a treatment beam to the object.

14. The method of claim 13, further comprising:
generating, based on the imaging dataset, an image associated with the object, wherein the treatment beam is delivered to the object based further on the image.

15. The method of claim 14, the delivering of the treatment beam to the object further comprising:
adjusting a treatment plan based on the image; and
delivering, from the treatment head and based on the adjusted treatment plan, an adjusted treatment beam to the object.

16. The method of claim 14, the causing the treatment head to deliver a treatment beam to the object further comprising:
adjusting a treatment plan based on the image; and
causing the treatment head to pause the delivery of the treatment beam.

17. The method of claim 14, further comprising:
determining whether an unpredicted motion of the object exists based on the image; and
in response to determining that the unpredicted motion of the object exists, causing the treatment head to pause the delivery of the treatment beam.

18. The method of claim 14, further comprising:
determining whether the object has ceased a planned breathhold based on the image; and
in response to determining that the object has ceased the planned breathhold, causing the treatment head to pause the delivery of the treatment beam.

19. A system comprising:
a treatment assembly including a treatment head configured to deliver a treatment beam to an object and a first assistance assembly configured to facilitate a delivery of the treatment beam;
an imaging assembly including a first imaging radiation source configured to direct a first imaging beam toward the object, a first detector configured to detect at least a portion of the first imaging beam, and a second assistance assembly configured to facilitate a delivery of the first imaging beam;
a gantry having a rotation axis and supporting the treatment assembly and the imaging assembly, the treatment head, the first imaging radiation source, and the first detector being disposed on a same side, along the rotation axis, of the first assistance assembly and the second assistance assembly.

20. The system of claim 19, wherein the first imaging radiation source is positioned apart from the treatment head by a certain distance along the rotation axis such that the first imaging radiation source delivers the first imaging beam to image a first region of the object while the treatment head is delivering the treatment beam towards a second region of the object;

the first region relates to a motion of the second region; or the motion of the second region is determined based on an image of the first region.

* * * * *